(12) United States Patent
Schuurkamp et al.

(10) Patent No.: US 10,402,542 B2
(45) Date of Patent: Sep. 3, 2019

(54) MONITORING ACTIVITIES OF DAILY LIVING OF A PERSON

(71) Applicant: KONINKLIJKE PHILIPS N.V., Eindhoven (NL)

(72) Inventors: Gertjan Laurens Schuurkamp, Utrecht (NL); Rob Jaartsveld, Best (NL); Jan Hendrik Poesse, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 28 days.

(21) Appl. No.: 15/548,118

(22) PCT Filed: Feb. 11, 2016

(86) PCT No.: PCT/EP2016/052883
§ 371 (c)(1),
(2) Date: Aug. 2, 2017

(87) PCT Pub. No.: WO2016/131696
PCT Pub. Date: Aug. 25, 2016

(65) Prior Publication Data
US 2018/0025122 A1    Jan. 25, 2018

(30) Foreign Application Priority Data
Feb. 18, 2015   (EP) ..................................... 15155671

(51) Int. Cl.
*G06F 19/00*   (2018.01)
*H04H 20/93*   (2008.01)
(Continued)

(52) U.S. Cl.
CPC ........ *G06F 19/3418* (2013.01); *G06T 11/206* (2013.01); *H04H 20/93* (2013.01);
(Continued)

(58) Field of Classification Search
CPC .. G06F 19/3418; G06F 3/0484; G06T 11/206; G06T 2200/24; G06T 2210/41
See application file for complete search history.

(56) References Cited

U.S. PATENT DOCUMENTS 5,692,215 A    11/1997  Kutzik et al.
6,640,212 B1 * 10/2003  Rosse ................... G06F 19/325
                                                    705/7.13
(Continued)

FOREIGN PATENT DOCUMENTS

WO        2009138917 A2    11/2009

OTHER PUBLICATIONS

Andree Afonso, https://dribble.com/shots/1838560-Weather-App, Dec 8, 2014. (Year: 2014).*
(Continued)

*Primary Examiner* — Michelle L Sams

(57) ABSTRACT

Presented are concepts for monitoring activities of daily living, ADLs, of a person within an environment. Once such concept provides a graphical interface for an ADL monitoring system, wherein the graphical interface is adapted to display a graphical element representative of an ADL detected by the ADL monitoring system, and wherein the shape, size, position, orientation, pulsating and/or color of at least a portion of the graphical element is based on one or more attributes of the detected ADL.

28 Claims, 10 Drawing Sheets

(51) Int. Cl.
*H04N 21/81* (2011.01)
*G06T 11/20* (2006.01)
*G06Q 50/22* (2018.01)
*G06F 3/0484* (2013.01)

(52) U.S. Cl.
CPC ....... *H04N 21/8133* (2013.01); *G06F 3/0484* (2013.01); *G06Q 50/22* (2013.01); *G06T 2200/24* (2013.01); *G09G 2340/08* (2013.01); *G09G 2340/10* (2013.01)

(56) References Cited

U.S. PATENT DOCUMENTS

| | | | |
|---|---|---|---|
| 8,868,616 B1 | 10/2014 | Otto et al. | |
| 2005/0131318 A1 | 6/2005 | Peifer et al. | |
| 2005/0234310 A1 | 10/2005 | Alwan et al. | |
| 2008/0301571 A1* | 12/2008 | Herzog | G06Q 10/00 715/764 |
| 2013/0095459 A1* | 4/2013 | Tran | A61B 5/6816 434/247 |
| 2013/0117696 A1 | 5/2013 | Robertson et al. | |
| 2014/0155705 A1 | 6/2014 | Papadopoulous et al. | |
| 2014/0247155 A1 | 9/2014 | Proud | |
| 2014/0249853 A1* | 9/2014 | Proud | G06Q 50/24 705/3 |
| 2014/0331165 A1 | 11/2014 | Fang et al. | |
| 2015/0088457 A1* | 3/2015 | Yuen | A61B 5/6838 702/160 |
| 2016/0231909 A1* | 8/2016 | Olsson | G05B 23/0272 |

OTHER PUBLICATIONS

"Fitbit Dashboard Updated With Weekly Activity and More", https://web.archive.org/web/20141123074834/https://blog.fitbit.com/fitbit-dashboard-updated-with-weekly-activity-and-more/, Nov. 23, 2014. (Year: 2014).*

"Fitbit Log in", https://www.fitbit.com/login, Sep. 28, 2009. (Year: 2009).*

Dadlani et al: "Aurama: Caregiver Awareness for Living Independently With an Augmented Picture Frame Display"; AI & SOC (2010) 25:233-245.

Pirsiavash et al: "Detecting Activities of Daily Living in Firs-Person Camera Views"; IEEE, 2012, pp. 2847-2854.

Ropinski et al: "Survey of Glyph-Based Visualization Techniques for Szpatial Multivariate Medical Data"; Computers & Graphics 35 (2011), pp. 392-401.

Vermeiren et al: "Detecting Human Motion: Introducing Step, Fall and ADL Algorithms"; eHealth 2009+, LNICST 27, pp. 62-69, 2010.

* cited by examiner

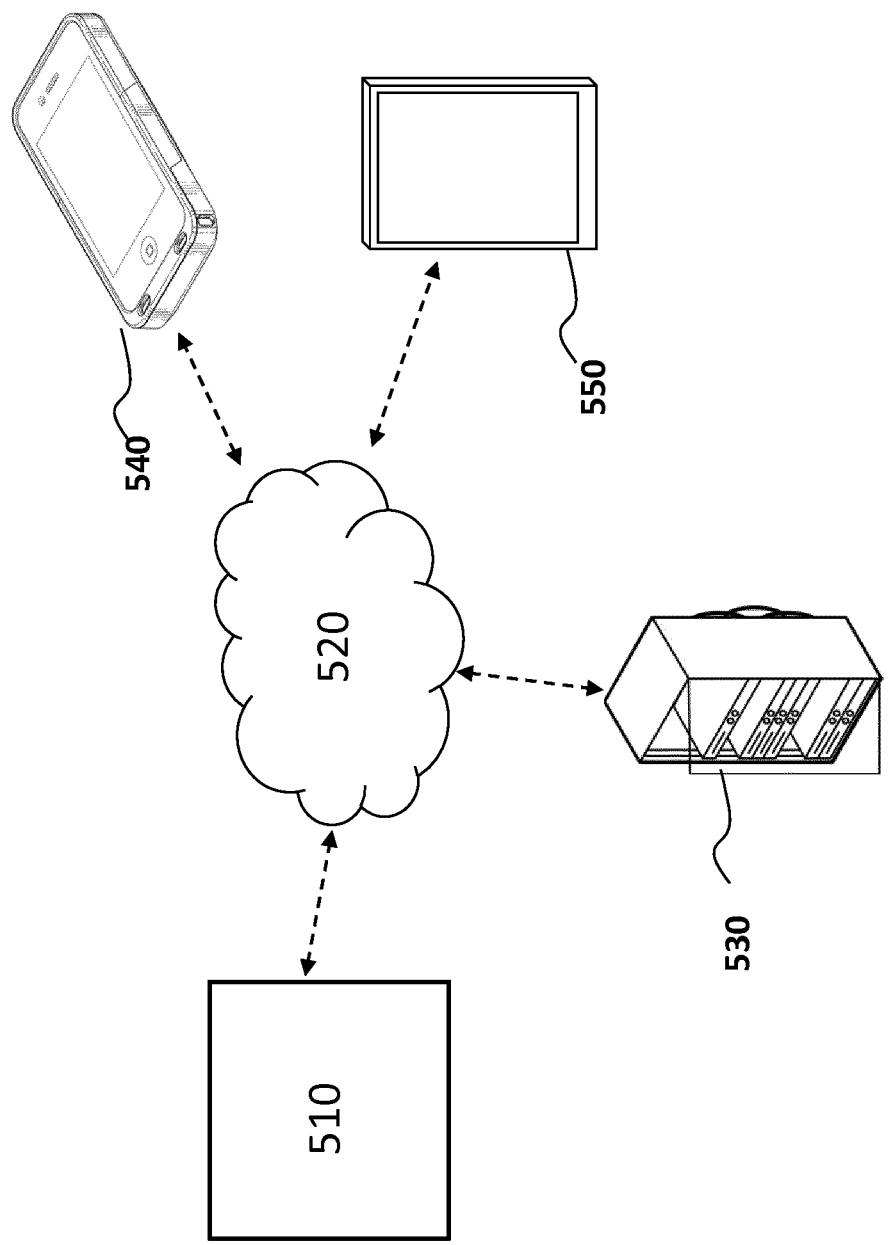

MONITORING ACTIVITIES OF DAILY LIVING OF A PERSON

CROSS-REFERENCE TO PRIOR APPLICATIONS

This application is the U.S. National Phase application under 35 U.S.C. § 371 of International Application No. PCT/EP2016/052883, filed on Feb. 11, 2016, which claims the benefit of European Patent Application No. 15155671.9, filed on Feb. 18, 2015. These applications are hereby incorporated by reference in their entirety herein.

FIELD OF THE INVENTION

This invention relates to monitoring activities of daily living (ADLs) of a person and more particularly to displaying, in a GUI, a graphical element that is representative of an ADL detected by an ADL monitoring system

BACKGROUND OF THE INVENTION

Functional assessment or monitoring of a person's health status, physical abilities, mental abilities, or recuperation after injury, hospitalization and treatment is of primary concern in most branches of medicine, including geriatrics, rehabilitation and physical therapy, neurology and orthopaedics, nursing and elder care.

Investigations have found that an individual's functional ability is actually environment-specific, since function increases when subjects are in familiar surroundings due to reduced confusion. Also, one-time assessment of function does not allow for assessment of variability of functional performance over the course of a day or several days, nor does it allow for assessment of change which is important in determining the adequacy of certain clinical services and treatments (such as rehabilitation) following functional loss.

A consensus therefore exists that it is preferable to assess or monitor independent functioning of a person at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they live independently in their own home or within familiar surroundings. For example, one such known system for detecting activities of daily living of a person comprises three main components: (i) a sensor system that senses and collects information about the person's activities and behaviours; (ii) an intelligence (or information processing) system that interprets the collected information for determination of ADL behaviour; and (iii) a user interface system that enables care givers to inspect the interpreted (processed) information. The intelligence system typically makes use of computational techniques known in the art as artificial intelligence. The system may be supported by conventional technologies for data collection, transmission, and storage.

In practice, however, a major difficulty is encountered by the wide range of variations that can happen in actual care cases. For example, people can live in differently architected houses, have different lifestyles and habits. Care givers may also have different needs, locations and/or lifestyles. Also, different people may have different care needs and so differing aspects of the activities and behaviours may be of interest for monitoring. Since there are so many possible circumstances, situations and contexts that can occur in daily life, it is difficult to capture any display information about them all in a manner which is quick and easy to interpret. Quick and easy interpretation is of paramount importance in providing good quality care by professional care institutions as well as personal care givers.

Also, the ever-increasing complexity in striving to cover all possible contexts and situations requires more elaborate and detailed information to be communicated to a user, carer, relative or healthcare professional. Thus, too much information may be presented to a viewer, thereby making assessment or understanding of ADLs difficult and/or time consuming.

SUMMARY OF THE INVENTION

The invention aims to at least partly fulfil one of the aforementioned needs. To this end, the invention provides methods, computer program products and systems as defined in the independent claims. The dependent claims provide advantageous embodiments.

Thus, the invention provides a method of and corresponding system for generating instructions for displaying a GUI on a display device using a processor device, which GUI is for monitoring of an ADL of a person within an environment and comprises a graphical element for representing the ADL, the graphical element being defined at least by a first graphical feature. In the method and system the data processor device is for performing the steps of: obtaining an attribute of the ADL; defining the first graphical feature; setting the first graphical feature based on the attribute of the ADL; generating the instructions for displaying the GUI.

The invention is based on the concept of display of a GUI including a graphical or visual element representative of a detected ADL of a person in a manner such that its appearance is based on an attribute of the ADL.

Activities of daily living concern basic activities that a person executes on a regular basis. Examples of activities of daily living are drinking, eating; cooking; medicating; sleeping; toileting; bathing; washing, leaving home or any kind of exercising such as walking, leisure activities such as reading or TV watching and many more etc. The invention provides ways to display and monitor such ADLs of a person over time in a simple and easy to understand manner.

Attributes of an ADL may comprise one or more of: the date and/or time and/or number of occurrence of the ADL; the duration of the ADL (per instance, or accumulated duration); the frequency of occurrence of the ADL; the time elapsed since a previous occurrence of the ADL; a rhythm of occurrences of the ADL; a moving average of the ADL; deviation of occurrences of the ADL from a predetermined pattern; a value of the ADL; a change in value of the ADL; a level of completion of the ADL and an importance level of the ADL, any and all may be determined within a (predetermined) time period and at any one point in time.

Thus, a GUI may provide a Visual representation of: ADL distribution over 24 hours, application of ADL intensity over 24 hour period, circular markers on time line, rectangular element indication duration (like sleep).

Obtaining an attribute of the ADL can mean obtaining earlier prepared such data from a database. Alternatively, in the invention obtaining such an attribute can comprise:

obtaining sensor signal data comprising a value, or a plurality of values, of a property of the person and/or the environment as detected for one or more points in time; and determining the attribute of the ADL.

Optionally, obtaining sensor signal data can comprise:

detecting a value, or a plurality of values, of a property of the person and/or the environment for one or more points in time In the invention one or more a graphical features of a graphical element can be defined or set to show up in the GUI. Examples of graphical features are: the shape, size, position, orientation, pulsation and/or colour. They may be based on one or more attributes of an ADL. In this way, behaviour of an ADL may be displayed in such a manner that a viewer can quickly and easily infer information about the ADL from one or more graphical features of the graphical element. This may enable a viewer to more easily identify and assess one or more detected ADLs and may enable space efficient organisation of a plurality of ADL data on a GUI as will be further highlighted herein below.

The invention may thus enable information about detected ADLs to be represented in a manner which helps to ensure that relevant details are shown or made easily identifiable. This may enable a viewer (such as a care giver) to quickly identify if a monitored person requires attention or assistance. The invention is also particularly useful in situations where multiple ADLs per person are monitored. And even more so in situations where multiple such persons are monitored. In these situations graphical interfaces easily become crowded with information, especially if that information includes considerable detail on the ADL. This may reduce/or even prevent quick and accurate assessment of a monitored person's situation.

Generating instructions for display of a GUI can mean generating a control signal for use by a display device. Such instructions can be in the form of simple images such as bitmap JPEG or other format. However, such instructions can also be more complex allowing real time buildup of the GUI or parts of the GUI on a regular display device such as for example CRT, LCD, OLED, Eink or other.

In the method the data processor device is performing the further steps of:

comparing the attribute of the ADL with a first threshold value;

setting the first graphical feature to a first feature value if the obtained attribute of the ADL is equal to or higher than the first threshold value, or;

setting the first graphical feature to a second feature value different from the first feature value if the obtained attribute of the ADL is lower than the first threshold value.

This enables setting of specific graphical features to have them indicate that a certain ADL deviates or has deviated from a regular pattern. Easy and fast spotting of such deviations is thus enabled.

The first and second values can be predetermined by the method or be user definable The comparison can be made for a plurality of attributes of an ADL and/or of a same attribute of a plurality of different ADLs. The comparison can be made continuously or periodically of purposes of timely update of the GUI data.

Additional options can be:

the data processor is performing the further steps of:

comparing the attribute of the ADL with a second threshold value that is higher than the first threshold value and, setting the first graphical feature to a third feature value different from the first and second feature values if the obtained attribute of the ADL is equal to or higher than the second threshold value, or setting the first graphical feature to the second feature value different from the first feature value and the third feature value if the obtained attribute of the ADL is lower than the second threshold value.

These additional options allow setting of multiple alert regimes for an ADL, such as normal, attention or warning.

In the method the data processor device can be performing the steps in a repeating fashion. This allows continuous or periodic update of attributes and GUI display.

The method can comprise:

the GUI comprising a plurality of graphical elements for representing the ADL at a plurality of different points in time, each one being defined at least by the first graphical feature and by a second graphical feature different from the first graphical feature;

the step of obtaining the attribute of the ADL can comprise obtaining the attribute of the ADL for each of the plurality of different points in time;

the step of setting the first graphical feature comprises setting this feature for the plurality of graphical elements such that each setting is based on the attribute of the ADL corresponding to a different one of the different points in time;

the data processor device is performing the further step of:

defining the second graphical feature;

setting the second graphical feature for the plurality of graphical elements such that for each particular one of the graphical elements such setting is based on the point in time corresponding to an attribute of the ADL upon which the setting of the first graphical feature of that particular element was based.

Time dependent information of an ADL is now enabled. This allows easy comparison of e.g. a current ADL state with historic ADL states over a certain period of time.

The method of the previous paragraph can comprise that:

the second graphical feature comprises a dimension of the graphical element, the plurality of graphical elements comprises a main graphical element which represents the attribute of the ADL corresponding to the point in time that is nearest to current time;

setting the second graphical feature comprises:

setting the dimension of the main graphical element to be larger than any dimension set for the other graphical elements of the plurality of elements.

This is one advantageous option for showing the time dependent data on the ADL. Now the attribute of an ADL is shown with different feature than the time dependency.

In the method each graphical element can be defined by a third graphical feature, and the plurality of graphical elements can comprise a main graphical element which represents the attribute of the ADL corresponding to the point in time that is nearest to current time;

the data processor device can be performing the step of:

defining the third graphical feature to be position in the GUI;

setting the position of at at least the plurality of graphical elements except the main graphical element such that they are arranged in the GUI in an array of graphical elements in the order of increasing or decreasing age with respect to current time of the attribute of the ADL they represent. Spatially distribution of graphical elements can further help to provide clarity and overview of the (historic) ADL data.

The method can comprise that
the processing device is performing the step of:
  setting the dimension of the graphical elements in the array to be equal to each other, or to be increasing in the order of decreasing age. This is for further providing clarity and overview of the data in the GUI.

The method can comprise that
the processing device is performing the step of:
  defining the array to be a linear array; and
  orienting the array row wise and positioning the array next to and either above, or below the main graphical element, or
  orienting the array column wise and positioning the array next to and either on the left or on the right side of the main graphical element. Yet even more clarity and overview is provided to the ADL data display.

The method can comprise that:
the plurality of graphical elements comprises a main graphical element which represents the attribute of the ADL corresponding to the point in time that is nearest to current time;
the attribute of the ADL comprises an average or cumulative value of the attribute over a period of time;
the data processor device is performing the further steps of:
  providing the attribute of the ADL represented by the main graphical feature also as an alphanumerical value. Now also detailed information on the most current ADL monitoring is provided.

The method can comprise that:
the GUI is for monitoring a plurality of ADLs of the person;
the data processor device is performing the steps of:
  obtaining an attribute of the plurality of ADLs of the person
  for each one of the plurality of ADLs, arranging the one or more graphical elements representing that one ADL to be positioned within an ADL GUI area (170. 170A 170B);
  positioning the different ADL GUI areas within the GUI area such that they do not overlap at least partially.

The method of the previous paragraph can comprise that:
the step of positioning the different ADL GUI areas comprises positioning the different ADL GUI areas within the GUI in either row or column orientation The confinement of ADL data to a limited area within a GUI allows display of multiple ADL data in a GUI screen, for different ADLs of one person, and/or for the ADLs of different persons. This provides a good GUI screen for overview of a care giver institution in charge of care of multiple persons.

The method can comprise
the data processor device comprising the step of:
  obtaining identification data for identifying the person and corresponding to the ADL represented by the graphical elements of the ADL;
  adding the identification data to the GUI to enable a user to identify the person that the graphical elements of an ADL belong to. Identification of the person is paramount e.g. for direct communication in case of alert, or for instructing care givers to go to a certain person.

The method can comprise displaying a GUI using a display device, wherein
the method comprises a method of any of the previous method claims;
the display device is performing the steps of:
  displaying the GUI using the generated instructions for displaying the GUI.

The method can comprise:
the data processor is performing the steps of:
  obtaining user input in the form of input device signal to switch from a first GUI screen comprising ADL data of a plurality of persons to a GUI screen showing ADL data of a particular one person of the plurality of persons, or to show ADL data of a particular one person of the plurality of persons in a further GUI window. With a pointer, steered using any kind of input device, and clicking on or hovering over a part of the GUI screen allocated to multiple ADL data or single ADL data of a particular person a GUI screen with more detailed ADL information of that person can be conveniently brought up.

The invention provides a computer program product downloadable from a communications network and/or stored on a computer readable medium and/or microprocessor-executable medium wherein the computer program product comprises computer program code instructions, which when executed on a computer, implement a method as claimed in any one of the method claims 1 to 14.

The invention further provides a system comprising a data processing device and the computer program product.

The independent claims define analogous advantages features for method and system claims. The advantages explained for the method herein above and herein below will also apply to the corresponding systems.

The system can comprise:
a server device comprising the data processor device and the configured to:
  transmit the generated instructions for display of the GUI to a client device or communication network. In this configuration all display instructions are made available by a server. A user can link with the server to work with the GUI.

The system can comprise:
a server device comprising the data processor device;
a client device comprising the display device;
wherein
the server device is configured to transmit the generated instructions for display of the GUI to the remote client device;
the remote client device is configured to receive the generated instructions for display of the GUI and to use the instructions to display the GUI.

The system can comprise:
a client device comprising the data processor device and the display device. This can be a standalone device either receiving ADL data or even further configured to work with raw sensor data if the processor is configured for that.

The data processing device may be remotely located from the display device, and the control signal may thus be communicated to the display device via a communication link. Such communication link can be e.g. is the internet and/or a wireless communication link. Other links are described herein below. In this way, a user (such as a care giver) may have an appropriately arranged display device that can receive and display information about ADLs of one or more persons that are remotely located from the user. Embodiments may therefore enable a user to remotely monitor the ADLs of a person using a portable display device, such as a laptop, tablet computer, mobile phone, PDA, etc.

The system may further comprise: a server device comprising the data processing device; and a client device comprising the display device. Dedicated data processing means may therefore be employed for the purpose of determining an attribute of the detected ADL, and generating a control signal, thus reducing processing requirements or capabilities of other components or devices of the system.

The system may further comprise a client device, wherein the client device comprises the data processing device and the display device. In other words, a user (such as a care giver) may have an appropriately arranged client device (such as a laptop, tablet computer, mobile phone, PDA, etc.) which undertakes processed received data in order to determine an attribute of the detected ADL and generate a control signal.

Thus, it will be understood that processing capabilities may therefore be distributed throughout the system in different ways according to predetermined constraints and/or availability of processing resources.

The step of generating display instructions may be further based on a display position of the graphical element.

The step of generating display instruction may be executed by a data processing device, that is remotely located from the display device. Thus, embodiments may further comprise the step of communicating the display instructions from the data processing device to the display device via a communication link.

The steps of generating display instructions may be executed by a client device.

There is provided a graphical interface for an ADL monitoring system for monitoring activities of daily living, ADLs, of a person within an environment, wherein the graphical interface is adapted to display a graphical element representative of an ADL detected by the ADL monitoring system, and wherein the shape, size, position and/or colour of at least a portion of the graphical element is based on one or more attributes of the detected ADL.

By way of further example, the expected frequency of the ADL 'preparing a hot meal' may be 'once a day', or '5 times a week', and a graphical element representative of this ADL every day may be displayed with a size that is proportional to the frequency. An irregularity in the frequency may then, for example, be that frequency has decreased and this may be easily perceivable by a viewer of the graphical interface seeing a reduction in size of a graphical element associated with the day for which the frequency has decreased. Further, if the frequency falls below a lower limit (e.g. an acceptable threshold), the colour of the graphical element may be set to a particular colour (e.g. red) which is indicative of an irregularity and thus easy for a viewer of the graphical interface to quickly identify and potentially act upon.

Alternatively, or additionally, a graphical element may be displayed such that its size is proportional to the nearness in time of the ADL. In other words, a graphical element representative of a current or most recently detected ADL may be displayed with a large size so that it is displayed with the most prominence, whereas a graphical element representative of a older detected ADL may displayed with a small size so that it is displayed with low prominence. Graphical elements representative of detected ADLs of the course of the previous week may therefore be displayed, wherein the graphical element for the current day are displayed with the largest size, and wherein the graphical elements for the rest of the week are displayed with a smaller size. Nearness in time may therefore be indicated by the size of a displayed graphical element.

There exist many sensors that can be employed by an ADL monitoring system. Typical sensors include PIR (Passive Infra-Red; measure movement and presence), OC (open-close; measure state of doors, in particular front doors, windows, and cupboards, including refrigerators), power sensors (measure current consumption of appliances, such as microwave, water cookers, TV, etc), and pressure mats (measure occupancy of user sitting in chair, lying in bed, standing on door mat in front of front door, etc). Many others exist and are conceivable, such as sensors to signal light switch state, or sensors that measure environmental conditions such as humidity, CO2 level (or CO and smoke), Particulate Matter level, etc. A further range of sensors are those based on physical quantities, such as accelerometers, magnetometers, gyroscopes, and air pressure sensors. Accelerometers, for example, can also measure state of doors and their open-close movements. Yet another range of sensors consists of microphones and cameras (including infra-red, or even UV and beyond, part of spectrum), to which also belong GPS and location-sensitive IR. Ultra-sound or RF-based sensors, including RFID tagging, provide additional input. Appliances having an own IP-address, known as the internet-of-things, provide further sensor input signals that can be taken by the smart-home system.

Although the sensor(s) may be mounted in the environment (e.g. the person's home), they may also be attached to user utilities (such as a keyring) or put in clothes, in a pocket or bag, or as insole or undergarment, etc. They may also be fabricated to be worn explicitly like a wrist watch or pendant. Further, the sensors may communicate their output signals via a wired or wireless connection, or a combination thereof.

The sensors may also be adapted to undertake primary processing of the detected values, such a signal filtering, sampling, conditioning, etc., so as to reduce required transmission bandwidth and/or transmission duration for example. Alternatively, the sensors can send raw data.

Non-intrusive monitoring may therefore be realized with relative simple sensors that provide data on specific ambient conditions or properties/parameters of the environment (such as temperature or humidity for example), or properties of the person (such as movement, for example). Such sensors for measuring ambient condition or properties/parameters of the environment may be simple, small and/or cheap. Also, the movement of the person may be detected with, for example, a Passive InfraRed (PIR) sensor which is a cheap component. Movement sensors may be used to switch on lighting and people are therefore typically familiar with their usage. Thus, ADL monitoring systems of the invention may employ sensors that are considered to be non-intrusive and more easily accepted by the monitored person. Yet, with the data provided by these sensors, ADLs may be determined and provide information on the person being monitored.

For example, with a humidity sensor and a movement sensor in the bathroom it may be inferred that the person is taking a shower. In a further example, with a temperature sensor and a movement sensor in the kitchen it may be determined that the person is preparing a hot meal. It is a further advantage that the sensors may be stationary sensors that are located for example in the bathroom and in the kitchen, thus making it unnecessary for the person to wear a device.

Indeed, a displayed graphical element may be devoid of alphanumerical characters (e.g. text and numbers). This may therefore enable the display of large amounts of information relating to detected ADLs without overwhelming the viewer with excessive and/or cluttered text and/or data.

The invention may therefore be used to dynamically update an ADL monitoring graphical display/interface based on one or more particular attributes of a detected ADL.

System of any one of claims herein the system is a client device in the form of a personal computer, laptop computer, notebook computer, tablet, mobile phone, smart phone, or other electronic device having an electronic display device.

BRIEF DESCRIPTION OF THE DRAWINGS

The invention will now be described in detail with reference to the following schematic drawings:

FIG. 5 is a block diagram of a system for monitoring ADLs of a person within an environment according to the invention;

DETAILED DESCRIPTION OF THE EMBODIMENTS

Figure 1:
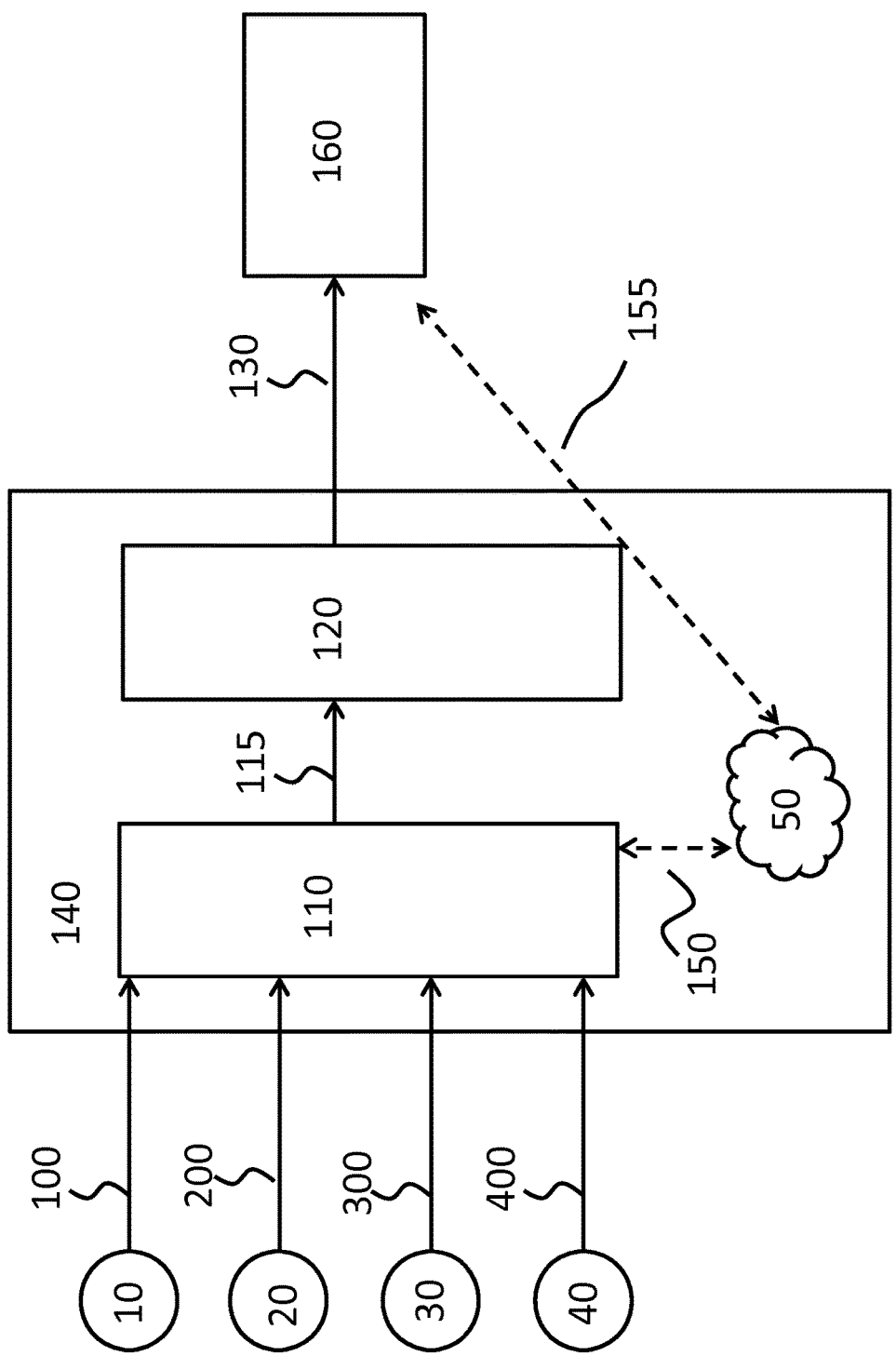
FIG. 1 is a block diagram of a system for monitoring ADLs according to the invention.

The invention concerns monitoring activities of daily living, ADLs, of a person within an environment. Persons that may be monitored may be persons with reduced mental abilities or awareness or reduced physical abilities. A persons monitored may be for example be, disabled persons, an elderly persons, an injured person, a medical patient, etc. Elderly persons can mean persons above 65 years, above 70, or above 80 years old.

The invention may be utilized in many different types of monitoring environments, such as a hospital, ward, care home, person's home, etc. The following description provides a context for the description of elements and functionality of the invention and of how elements of the invention can be implemented.

In general, to be able to observe changes in "normal" daily behavior of a person one may monitor ADLs of a person over time to spot deviations from patterns observed. I particular anomalies or irregularities can be of interest in many care situations. The type of anomaly or irregularity can be different per case. A large class of anomalies relate to aberrations in an ADL routine of the person. For example, an above average number of toilet visits during the night. More severe incidents form another class, for example falls by the person.

By way of example, ADLs may include:
(i) Medication
  a. Is the elder taking his medicine in proper way at proper moments?
  b. Is the elder taking the correct/prescribed medication?
(ii) Sleep
  a. Is the elder sleeping sufficiently and undisturbed?
(iii) Eating/Drinking
  a. Is the elder eating and/or drinking sufficiently and regularly?
  b. Does he prepare meals by himself?
(iv) Physical activity
  a. Is the elder active during the day?
  b. Is there little sedentary behaviour?
(v) Toileting
  a. Is the elder toileting in normal way?
  b. Are there frequent visits to the toilet during the night?
(vi) Bathing
  a. Is the elder bathing adequately?
(vii) Being In/Out House a. Is the elder going out?
(xiii) Ambient climate a. Is the environment "clean"? b. E.g., is temperature proper, is the $CO_2$ level healthy, is the particle (PM) level healthy?
(ix) Etc.

Based on the above exemplary ADLs, the following examples of anomalies, irregularities or warnings/alerts may relate to:

A. Sign of activity, or sign of inactivity
B. Presence in rooms considered risky (e.g. alone in kitchen when elder suffering dementia)
C. Leaving the house at unexpected moments, such as during the night
D. Exceptional frequency or exceptional duration of toilet visits
E. Exceptional duration of bathing
F. Sleeping shorter
G. Reduced activity
H. Etc.

The present invention is therefore directed toward enabling information about detected ADLs of a person to be displayed and monitored. Further, the invention is to display the ADL information with simplicity and accurate organisation while providing, or provide further easy access to, enough detail so that that care giver(s) are facilitated to quickly and with increased efficiency and/or reliability observe anomalies in daily behaviour of the person monitored. The displayed information may be used to identify or indicate that the person is in need of help, for example. It is a further goal of the invention to enable such display of information for multiple ADLs per person and for multiple persons in clear overview.

In the invention the following terms and definitions are used.

A graphical user interface (GUI) is a type of interface that allows users to interact with electronic devices through graphical icons and visual indicators such as secondary notation.

A display device is an electronic display device that can be controlled by a display control device. The display control device can be part of, or operate together with, a processor device.

Generating instructions for displaying a GUI can comprise (or be as simple as) constructing images (Bitmap, JPEG, Tiff or the like) of GUI views to be displayed on a display device using regular methods known in the art. Alternatively, such generation of instructions can comprise more dedicated instructions for real time buildup of a GUI view. The instructions can be in the form of a display control signal.

The invention is at least partly based on the insight that it is advantageous to use information about the attribute(s) of a detected ADL to define or control the display of one or more graphical elements of a GUI. In particular one or more graphical features of the graphical elements can be seet according to attributes of an ADL. In other words, an attribute of a detected ADL may be used to alter the appearance of graphical elements by way of altering the graphical features.

Graphical features can be for example be chosen from the group of: spatial location/position (or relative mutual location/position in case there are multiple graphical elements) of the graphical element(s) in a GUI area, orientation, size (dimensions such as height width length and/or area size), shape (outline shape), shape fill (hatching, shading or the like), colour, contrast, hue, display frequency (continuous or blinking with a specified frequency). Unless otherwise specified in the description or the claims, the first graphical feature and the second graphical feature or other graphical features can be independently chosen from the above group. Preferably, the second graphical feature is the area size of the graphical element. Preferably, the first graphical feature is area colour or outline shape. Preferably the graphical element(s) have a shape with rounded corners such as rectangular shape with rounded corner, circular shape or oval shape. This gives a GUI appearance, especially when a plurality of ADL areas is present in the GUI view. Thus, if the first graphical feature is colour, the first, second and third predetermined values are different colours.

They invention may thus employ the concept that the appearance of a graphical element of a display may be determined based on an attribute of an ADL inferred or detected by an ADL monitoring system. A viewer of such graphical elements may therefore infer information from the appearance of the graphical elements, even when they are devoid of any text, numbers, or alphanumeric characters for example. By way of example, visual comparison of the graphical elements graphical features may provide or imply relative information about one or more attributes of detected ADLs, thus enabling simple and quick inference of information about the detected ADLs by a viewer. Graphical elements of a certain colour, for example, may identify detected ADLs exhibiting anomalies or irregularities, and may therefore be quickly and easily identified amongst a display comprising a high number of graphical elements. Also, large graphical elements may relate to current (e.g. real time) ADLs, or historic ADLs that are nearest in time with respect to current time, whereas smaller graphical elements may relate to older (e.g. past) ADLs. In this way, up-to-date or most recent information may be displayed in a more prominent manner, whilst older information is displayed less-prominently so as to reduce visual clutter.

The appearance of graphical elements may be adapted in many ways in order to indicate one or more attributes of ADLs. By way of example, the following appearance characteristics (graphical features) may be indicative of various ADLs attributes as detailed respectively:

Shape: 1) Normal situation, 2) Irregular situation, 3) Transition situation, 4) Immediate attention situation, where 1 to 2 relate to different shapes such as ssquare, circular triangular etc;

Size: 1) Distance in time, 2) current day, 3) duration of the event, 4) combined time events;

Pulsation: 1) Blinking, 2) Blinking between two levels, 3) Pulsating in gradually increasing brightness and then decreasing it again to the same level;

Colour: 1) normal, 2) Notifications, 3) Alerts, where 1 to 2 denote different colours such as 1: blue, 2 yellow, 3 red;

Orientation: 1) Horizontal, 2) 90 degrees turned, 3) 180 degrees turned

The graphical features used in the GUI can be predefined or can be user defined. For the latter purpose, the invention may employ a step where a user is enabled to provide graphical feature definition input using a user input device.

In the invention, a user input device can be one or more of the following: a keyboard, mouse or other screen pointer device, touch sensitive display screen, speech recognition device or any other means known in the art.

ADL events may be detected or inferred from sensor output signals and there already exist systems and methods for such ADL detection or inference. Accordingly, the proposed concepts may be used in conjunction with existing ADL detection or monitoring systems/methods. For example, Dries Vermeiren et al describe a system based on 2 tri-axial accelerometers to detect the ADLs of a patient in a paper entitled "Detecting Human Motion: Introducing Step, Fall and ADL algorithms". Also, H Pirsiavas et al describe algorithms for detecting ADLs in first-person camera views in paper entitled "Detecting activities of daily living in first-person camera views" (CVPR, 2012). Because many such ADL detection or monitoring methods/systems are known and any one or more of these may be employed, detailed description of such methods/systems is omitted from this description.

The ADL can be one or more of the following: eating, drinking, sleeping, toileting, medicating, bathing, washing, exercising, and relaxing. Other ADLs can of coarse also be monitored, but the specified group is an important one for monitoring healthy living of the person monitored.

The attribute of the can be as defined herein before. All of these can be inferred for a (predetermined) time period, i.e. determined as averages or cumulative numbers within such period. Such time period can be 12 hours, 24 hours, 5 natural days or 7 natural days, a week, multiple weeks, a month or even a year. Preferably the predetermined time period is 24 hours, a week or a month. Each of the periods can have associated with it a time stamp, relating to when the attribute was determined. The time stamp may be in regular time measuring units and or date of a day, month or year.

In the system of FIG. 1 a plurality of sensors 10, 20, 30, 40 is arranged to measure a property of at least one of: a person; and the environment in which the person is and performs actions.

In this example, the first sensor 10 is one adapted to detect a value of an ambient condition parameter of the environment, such as temperature or humidity for example. The second sensor 20 is a movement sensor 20 adapted to detect movement of the person that is monitored. The third sensor 30 is a power sensor 30 adapted to detect a value of the power consumption of an electrical appliance used by the person within the environment. The fourth sensor 40 is an open/close sensor 40 adapted to detect the opening or closing of a door or a device, such as a fridge, storage cupboard, or cooker fore example. The first 10, second 20, third 30 and fourth 40 sensors are adapted to output first 100, second 200 third 300 and fourth sensor output signals, respectively, which are representative of the detected value(s) for the properties measured. Of course, many more sensors for many other properties may be employed so as to provide signals indicative of the environment and/or the person's movement/activities.

Some of the sensors can be preinstalled in the environment. They can have fixed location on walls, in the respective devices etc. Other sensors can be left mobile, for example if they need to be worn or carried by the person. Sensors may be part of existing communication devices such as electronic or smart watches, mobile phones, computers, tablets or the like.

The sensors 10, 20, 30, 40 are configured to communicate their output signals 100, 200, 300, 400 via a wired or wireless connection to a data processor device 140. By way of example, the wireless connection may comprise a short-to-medium-range communication link. For the avoidance of doubt, short-to-medium-range communication link should be taken to mean a short-range or medium-range communication link having a range of up to around 100 meters. In short-range communication links designed for very short communication distances, signals typically travel from a few centimeters to several meters, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), Near Field Communication (NFC), RFID, 6LoWPAN, UWB, Wireless HART, Wireless HD, Wireless USB, ZigBee. Examples of medium-range communication links include Wi-Fi, ISM Band, Z-Wave.

Here, the output signals are not encrypted for communication via the wired or wireless connection in a secured manner. However, it will be appreciated that one or more encryption techniques and/or one or more secure communication links may be employed for the communication of signals in the system to protect personal data of a person monitored.

The data processor device 140 further comprises an ADL inference unit 110 adapted to receive the first 100 to fourth 400 sensor output signals, to infer or detect an ADL of the person based on the received sensor output signals and to determine at least one attribute of an ADL. For this purpose, the ADL inference unit 110 may communicate with one or more data processing resources. In this case such resource is one available in the internet forming a so called "cloud" 50. Such data processing resources may undertake part or all of the processing required to infer or detect an ADL of the person based on the received sensor output signals. Thus, the embodiment may employ distributed processing principles using distribution of the data processor device over the cloud 50, ADL inference unit and/or client device.

The data processor device 140 by means of the ADL inference unit 110, is further adapted to an ADL output signal 115 representative of an attribute of an ADL. In other words, after having infered or detect an ADL of the person based on the received sensor output signals (either with or without communicating with data processing resources via the internet or "cloud"), an ADL output signal 115 representative of an ADL of the person is generated.

The data processor device further comprises a part 120 that is configured to use the output signal 115 to generate instructions (possibly in the form of a display control signal) 130 for display of a graphical user interface (GUI) on a display device 160 for providing the ADL information to one or more users. The signals 115 and/or 130 can be transmitted via wired or wireless connection. The wireless connection may be chosen according to examples described hereinabove for transmission of the sensor signals 100 to 400.

However, where the system, has made use of data processing resources via the internet or cloud 50 through connection 150, an output signal 155 may be made available to the display device 160 via the internet or cloud 50. In that case the data processor part 120 is effectively incorporated in the cloud 50 and instructions 130 can be similar to the instructions 155.

Figure 2:
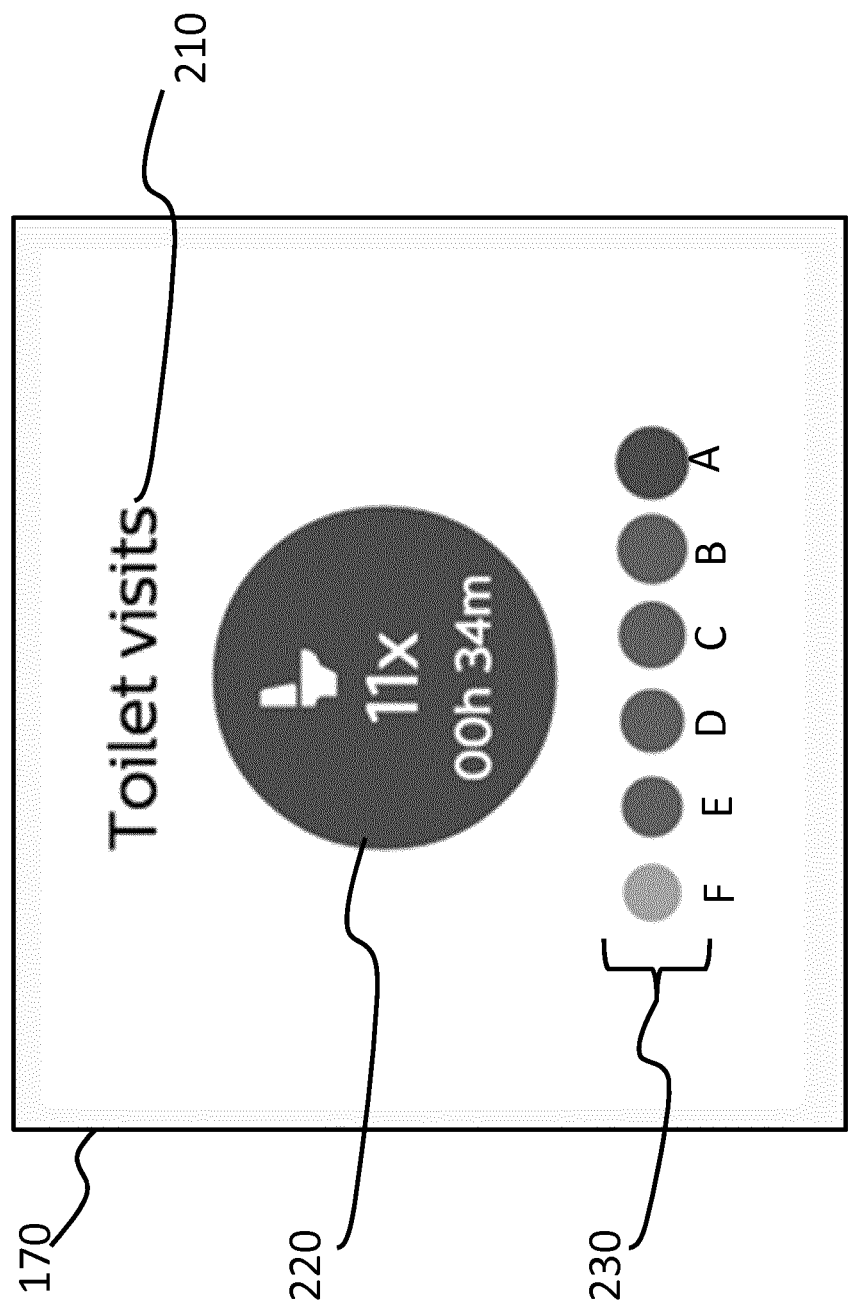
FIG. 2 is an exemplary displayed view of a GUI according to the invention.

FIG. 2 is an exemplary view of the GUI 180 as displayed on the display device 160 of FIG. 1. The GUI area 170 is adapted to display graphical elements in the GUI are area 170. Because the GUI is at least partly displayed on a display device, a GUI area is effectively also a display area. In this example, first 210 to third 230 graphical elements are displayed in the GUI area 170.

The first graphical element 210 comprises text providing a description of an ADL that the second 220 and third 230 graphical elements are representative of In this example, the text is "Toilet visits", thus indicating the second 220 and third 230 graphical elements relate to the number of toilets visits the monitored person has been detected as taking.

The second graphical element 220 comprises a (relatively) large circle containing a symbol representing a toilet. The circle also contains a number "11×" indicative of the cumulative number of toilets visits the monitored person has been detected as taking during the currently elapsed part of a predetermined timeframe. The time frame in this case is 24 hours, but can be a day, night or week, month or other. Thus, one attribute of the ADL is the number of toilet visits. Another attribute of the ADL is the amount of time that has elapsed since the monitored person previously visited the toilet. This attribute is in this case shown as the alpha numeric representation "ooh 34" beneath the number of toilet visits.

The third graphical element 230 comprises a plurality of sub graphical elements 230A, to 230F in the form of six circles and is positioned below the second graphical element 220. Each of the graphical elements 230A to 230 F is representative of the number of toilets visits the monitored person has been detected as taking during predetermined time periods elapsed before the one of graphical element 220 (e.g. previous 24 hours, days, nights, weeks or months). It can be seen that of the plurality of graphical elements 230 the size reduces upon going from the element 230A to 230F. This is because the graphical feature size has been made dependent or is based upon the time stamp of the elapsed predetermined period such that the size becomes smaller for older ones of the attribute of the ADL. Such ranking in time can alternatively also be done using numbers. In that case size of the circles in graphical element 230 can be kept equal. This however tends to clutter or reduce clarity of the ADL representation in the GUI area 170 considerably.

Thus, the second 220 and third 230 graphical elements are displayed such that their size is representative of the nearness/proximity in time of the ADL (visiting the toilet). In other words, a second graphical element 220 representative of a current day is displayed with a large size so that it is displayed with the most prominence, whereas the third graphical elements 230 representative of preceding (e.g. older) days are with a small size so that they are displayed with less prominence. Graphical elements representative of detected toilet visit over the course of the week are therefore displayed, wherein the second graphical element 220 (which is representative of toilet visits for the current day) is displayed with the largest size, and wherein the third graphical element 230 (which is representative of toilet visits for the preceding six days of the week) is displayed with a smaller size.

As described hereinbefore, in the current example, the second graphical feature of the graphical elements 220 and 230 is their size which in this example is chosen to be representative of the time stamp of an attribute of the ADL. A first graphical feature different form size of the graphical elements is chosen to be their color. Thus, the second and third graphical elements are displayed such that their colour is representative of the attribute of the ADl that is the number of occurrences of the ADL (visiting the toilet). In other words, the second 220 and third 230 graphical elements are displayed with a colour that depends on the number of detections of the ADL for their respective time period. More specifically, in this case it is specified that if the number of toilet visits is above a certain predetermined threshold value, the colour becomes yellow, while an attribute of the ADL beneath that threshold invokes a blue as the colour. Furthermore, if the attribute of the ADL is higher than a second threshold value, which is higher than the first threshold value, the colour of the element is set to red. The colours indicating: different alert states: blue (normal), yellow (attention), red (warning). The number of thresholds can be less or more and defined according to use together with other value judgements. Thus in this example it is observed that each circle of the third graphical element 230 comprises a particular colour (F is yellow; A and the circle of 220 are red and the rest is blue) that is indicative of the cumulative number of toilets visits the monitored person was detected as taking during its associated/respective predetermined time period.

The darkness of the colour increasing in proportion with the cumulative number of toilets visits could have been used as alternative to the colour. Also shading could have been used.

From the colours, time periods (in this case days) during which the number of toilet visits is abnormally high or low may be quickly and easily identified, since the respective graphical element(s) will be of a lighter or darker or different colour than the other graphical elements and therefore more prominent in the user's vision. Graphical elements representative of detected toilet visit over the course of the week are therefore displayed, wherein the graphical elements (which are representative of toilet visits for a respective day) are displayed with a colour indicative of a numerical value or range. A numerical value or range is therefore indicated by the colour of a displayed graphical element.

The element 220 comprises a graphical icon identifier representing toileting. This is beneficial for quick assessment, but is not needed. If it is present, then element 210 may be omitted without preventing the ability of direct recognition of the ADL in question. Especially when multiple ADLs need be shown in one view of the GUI, this may be advantageous for maximising the number to be shown while minimising clutter of data.

Thus, if the second graphical element 220 relates to a current day being Sunday, the six circles of the third graphical element 230 respectively relate to the preceding individual days of Saturday, Friday, Thursday, Wednesday, Tuesday and Monday. It will therefore be appreciated that the displayed graphical elements of FIG. 2 display information relating to history of a monitored person's ADL of visiting the toilet over the course of a current day and the preceding six days.

Scrolling through different time period data can be done and implemented as for views described in FIGS. 3 and 4.

The graphical elements are located or positioned close to each other in the Gui area 170. In this case, elements 210, 220 and 230 are stacked while the smaller ones of element 230 are arranged in a row (horizontal in the FIG. 2). This gives a compact area 170 that comprises both detailed current information compared to historic information on an ADl of a person. The row of elements 230 can also be located above the element 220 or 210. Alternatively, the row 230 can be arranged as a column vertically at either side of the element 220, without deteriorating small and concise representation of the data.

The area 170 made up this way is suitable for arranging multiple of similar ADL areas 170 in a row on another GUI view. Analogously, if multiple of ADLs need to be arranged in columns, an area can be filled by arranging the element 230 in horizontal rows on either side of the element 220. Hence the area can have smaller height than width. Benefits will be described herein below.

In this example the elements have circular shape. Other shapes can also work like rectangular square etc. However, circles may be of preference for reasons also explained further below. Shapes preferably have rounded corners as with circles ovals or rounded rectangles and triangles. Alternatively shapes can comprise rectangles, squares, triangles trapezoids diamonds etc.

Preferably for two consecutive graphical elements in time and most preferably for all of the plurality The Plurality of graphical elements can be connected to form one continuous graphical element. For example, the continuous graphical element can be a bar with gradually changing height and/or width and/or colour. Alternatively it may be a pychart type element of any form. Preferably, in view of increased clarity, at least two, but preferably all of the plurality of graphical elements are separated from one another to form single individual graphical elements.

With the above graphical elements setup, a viewer receives detailed information of an ADL at one particular time, as well as history of the ADL within a (limited) period of time. In particular, the history of the ADL deviations from average patterns of pre-set values remains visible through the highlighting with colour. Further, since all circles are located in a confined area, the set of elements allows a quick assessment of the situation with respect to the ADL in one glance without having to search or scan a larger area. Further, such display of information also allows efficient grouping of ADLs per person and of multiple such persons in one GUI display. Hence, a viewer can have situational awareness with regard to one or more ADLs of a person for a number of persons monitored at one glance at the screen. This will also be described further below.

Figure 3A:
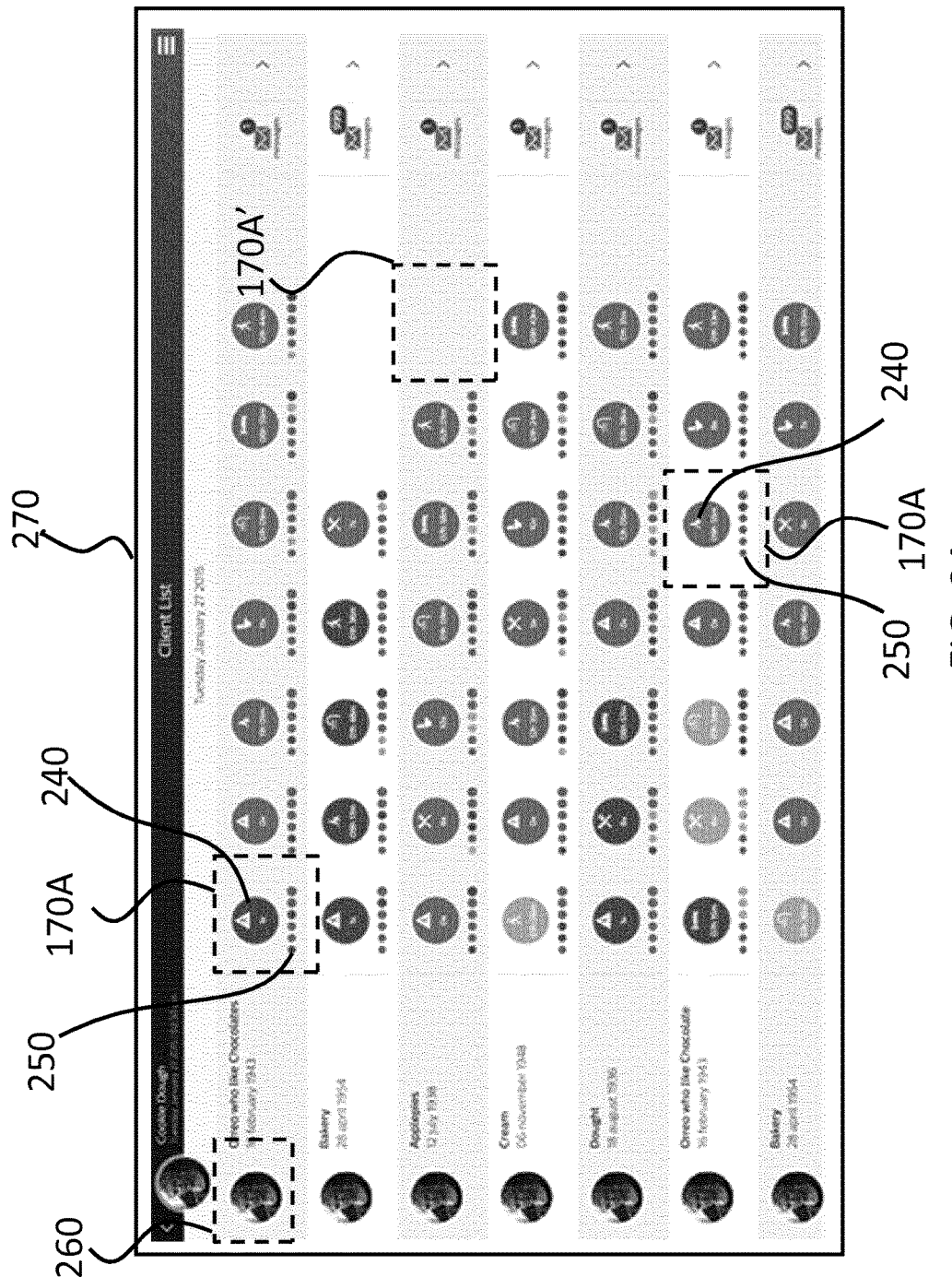
FIG. 3A is another exemplary displayed view of a GUI according to the invention.

FIG. 3A is another exemplary view of a GUI area 270 provided by the display 160 of FIG. 1. Here, the GUI area 270 comprises plurality of GUI areas 170A where each of the areas 170A is identical and built up similar to the display area 170 depicted in FIG. 2. The elements 210 in FIG. 2 have been omitted from the areas 170A to reduce data clutter.

Each area 170A relates to a respective ADL and comprises first 240 and second 250 graphical elements for example as defined in FIG. 2. Hence all information representation advantages associated with a GUI area 170 is present for each of the ADLs shown.

The GUI areas 170A are displayed in rows, wherein each row is associated with a particular monitored person. Each row comprises a plurality of sub-display areas 170A, each comprising graphical elements representative of a respective ADL for the monitored person identified in Gui area 260. Thus, per person in this case 7 ADLs can be simultaneously shown in the GUI view. Information regarding multiple ADLs over a time period of a week, for example, is therefore displayed in a row associated with a monitored person. For row-wise grouping of ADLs of a person monitored, it is advantages in terms of use of display area to have the elements 230 as a horizontally (in the row direction) extended line of circles below or above the element 220 or as a vertical stack of circles on the left or right side of the element 220 as described hereinbefore. Alternatively, the ADLs of a person could be displayed in columns. This can be done using the same area 170 layout as described above, but it may be advantages to have the element 230 at the sides of element 220 and extended along the horizontal direction. In that way the area height becomes smaller allowing for more ADLs to be arranged in rows.

In the GUI configuration for FIG. 3A, the provision of multiple such rows (or of columns) of ADL per person therefore enables information regarding multiple ADLs over a time period to be displayed for multiple monitored persons. The GUI view of FIG. 3A can be regarded as a client list directly suitable for monitoring their ADL behaviour.

A viewer of such GUI view may therefore infer information from the appearance of the graphical elements, even where they are devoid of any text, numbers, or alphanumeric characters (as is the case for the second graphical element 250 of each sub-display area 170A). For example, visual comparison of the colour of the graphical elements may provide or imply relative information about one or more attributes of detected ADLs for one or more monitored persons, thus enabling simple and quick inference of information about the detected ADLs by a viewer.

Graphical elements of a certain colour, for example, may identify detected ADLs exhibiting anomalies or irregularities, and may therefore be quickly and easily identified amongst a relatively high number of displayed graphical elements. Also, large graphical elements relate to more recent or current (e.g. real time) ADLs, whereas smaller graphical elements relate to older (e.g. past) ADLs. In this way, up-to-date or the most recent information is displayed in a more prominent manner, whilst older information is displayed less-prominently so as to reduce visual clutter in the view of FIG. 3A.

In the GUI view of FIG. 3A, prioritization of ADLs monitored can be done. For example, if no deviations from averages or patterns during one week were detected for a certain ADL, then that ADL is not shown in the list (row or column of a person). Thus, in terms of the ADL of FIG. 2, when the colours of all elements 220 and 230 are blue (normal), then that ADL is not shown. This reduces clutter of data as in this way only ADLs that deviate from a certain normal behaviour are shown. In FIG. 3A it can be seen that area 170A' is empty, accounting for the fact that one ADL monitored apparently did not deviate over the total time period represented by the ADL area. In the second row two such ADLs have not deviated and are thus not shown.

Further, the GUI can include steps to change the order of persons according to the ADL behaviours in order to allowing a care giver to spot the urgent cases in the quickest way. Thus, in this case, the number of ADLs per person with any specific colour can be compared and used to decide that the person with the highest number is put on top of the list in the view of FIG. 3. Also a ranking of importance of ADL (e.g. eating/drinking being more important than showering) can be used. Other constraints and comparisons can be used to change order of showing persons or ADLs.

Figure 3B:
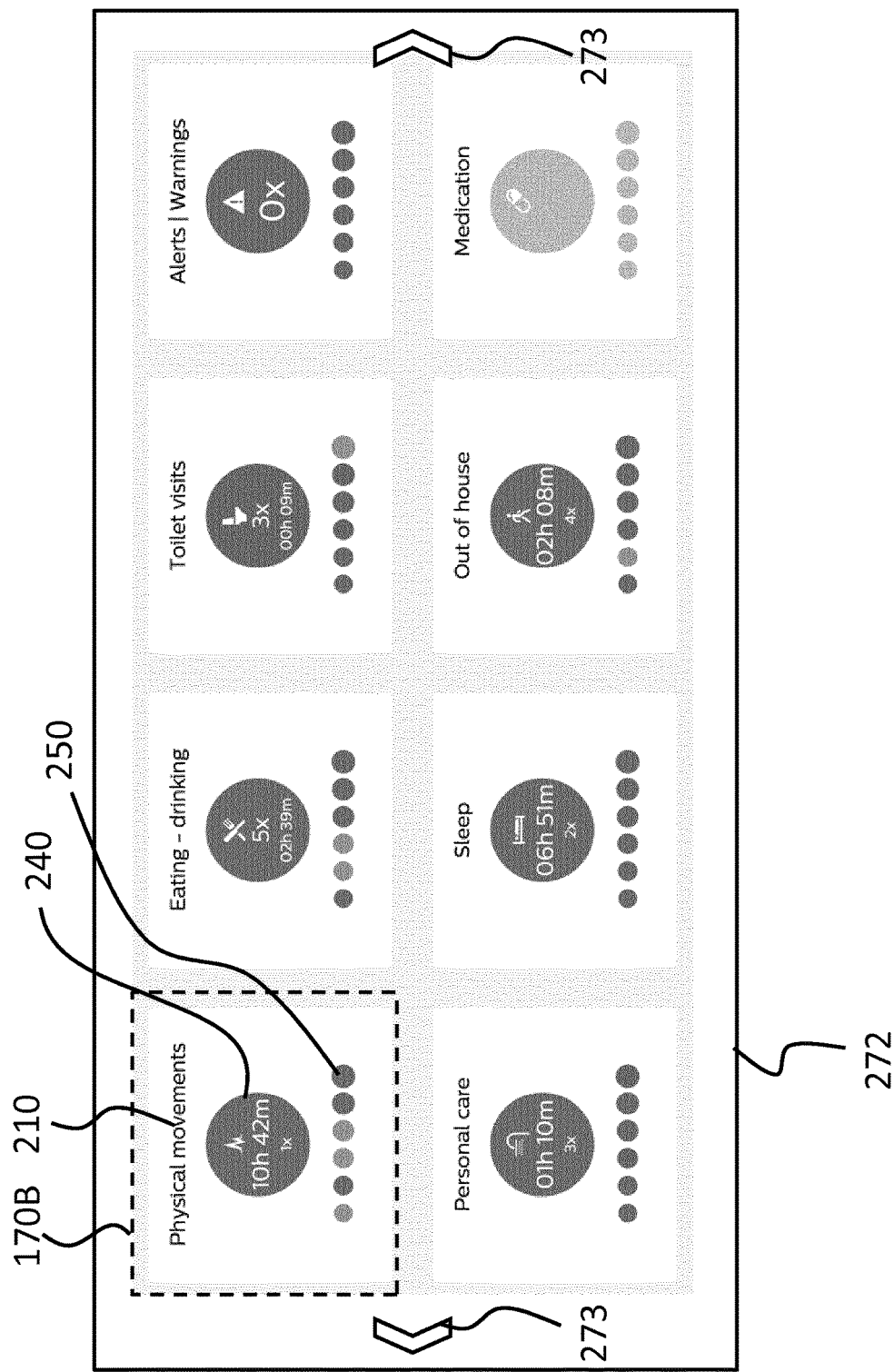
FIG. 3B is another exemplary displayed view of a GUI according to the invention.

FIG. 3B is another exemplary view of a display area 272 provided by the GUI 180 of FIG. 1. As described above, the display area 272 is adapted to display graphical elements in the display area 272. Here, the display area 272 comprises plurality of GUI area 170B, wherein each sub-GUI area 170B is similar to the display area 170 depicted in FIG. 2.

More specifically, each sub-GUI area 170B relates to a respective ADL on a monitored person and comprises a written description 210 of the ADL positioned above first 240 and second 250 graphical elements. The graphical elements are similar to the ones described with respect to FIG. 2. Thus, the first graphical element 240 comprises a (relatively) large circle containing a symbol representative of the associated ADL and an alphanumeric representation of an attribute of the ADL. The second graphical element 250 is positioned below the first graphical element 240 and comprises six circles, each representative of the attribute of the ADL for six preceding time periods (e.g. preceding days of the week). Each circle of the second graphical element comprises a particular colour that is indicative of the attribute in its associated/respective timeframe.

As with the example depicted in FIG. 2, the first 240 and second 250 graphical elements are displayed such that their size is representative of the nearness/proximity in time of the ADL. Thus, the first graphical element 240 representative of a current day is displayed with a large size so that it is displayed with the most prominence in the sub-display area 170A, whereas the second graphical elements 250 representative of preceding (e.g. older) days) are displayed with a small size so that they are displayed with less prominence.

Graphical elements representative of a respective ADL over the course of the week are therefore displayed by each sub-GUI area 170B. Also, graphical elements of each sub-GUI area 170B are displayed such that their colour is representative of an attribute of the associated ADL. In other words, the first 240 and second 250 graphical elements of each sub-display area 170 are displayed with a colour that depends on an attribute of the ADL for their respective time period. Thus, days during which the attribute has an abnormal value may be quickly and easily identified, since the respective graphical element(s) will be of differing colour from the other graphical elements and therefore more prominent in the user's vision.

The GUI area 170B for the monitored person are displayed in two rows. Information regarding multiple ADLs for a monitored person over a time period of a week, for example, is therefore displayed. The provision of multiple GUI area 170B therefore enables information regarding multiple ADLs over a time period to be displayed for a single monitored person.

A viewer of such graphical elements may therefore infer information from the appearance of the graphical elements, even where they are devoid of any text, numbers, or alphanumeric characters (as is the case for the second graphical element 250 of each sub-GUI area 170B). For example, visual comparison of the colour of the graphical elements may provide or imply relative information about one or more attributes of detected ADLs for one or more monitored persons, thus enabling simple and quick inference of information about the detected ADLs by a viewer.

As displayed in the display area 272 of FIG. 3B are scroll handles 273 for scrolling through the displayed graphical elements. In this way, a viewer may scroll through the ADLs of different monitored persons. For example, if the multiple ADLs for a monitored person over a time period of a week, for example, are displayed as shown in FIG. 3B, activating (e.g. clicking or selecting) either of the scroll handles 273 may cause the displayed graphical elements to change such that the multiple ADLs to be navigated for different time periods, (e.g. previous or next days, weeks, months, etc.). The GUI 160 therefore enables a user to navigate through ADL information.

Although it has been explained that the scrolls handles 273 enable a user to scroll through ADL information for different time periods, alternative arrangements may enable ADL information for different monitored persons (e.g. Persons assigned to be observed by the user of the system) to be navigated (e.g. scrolled through).

It is also noted that the GUI 180 may be adapted such that the display area 272 depicted in FIG. 3B is accessed by clicking on a link or icon 260 in the display area 270 depicted in FIG. 3A. In this way, the display area 272 depicted in FIG. 3B may be understood to be a sub-screen (or lower level display) which displays information about ADLs of a monitored person in more detail. Thus, if a user, when viewing the display area 270 of FIG. 3a, wishes to view more detail about the person associated with the top row of graphical elements, for example, selecting or clicking the link/icon 260 in FIG. 3A would result in the display area 272 of FIG. 3B being displayed. Information may therefore be arranged and displayed in a hierarchical manner, wherein levels of the hierarchy can be accessed/viewed via adjacent displays in the hierarchy.

Figure 4A:
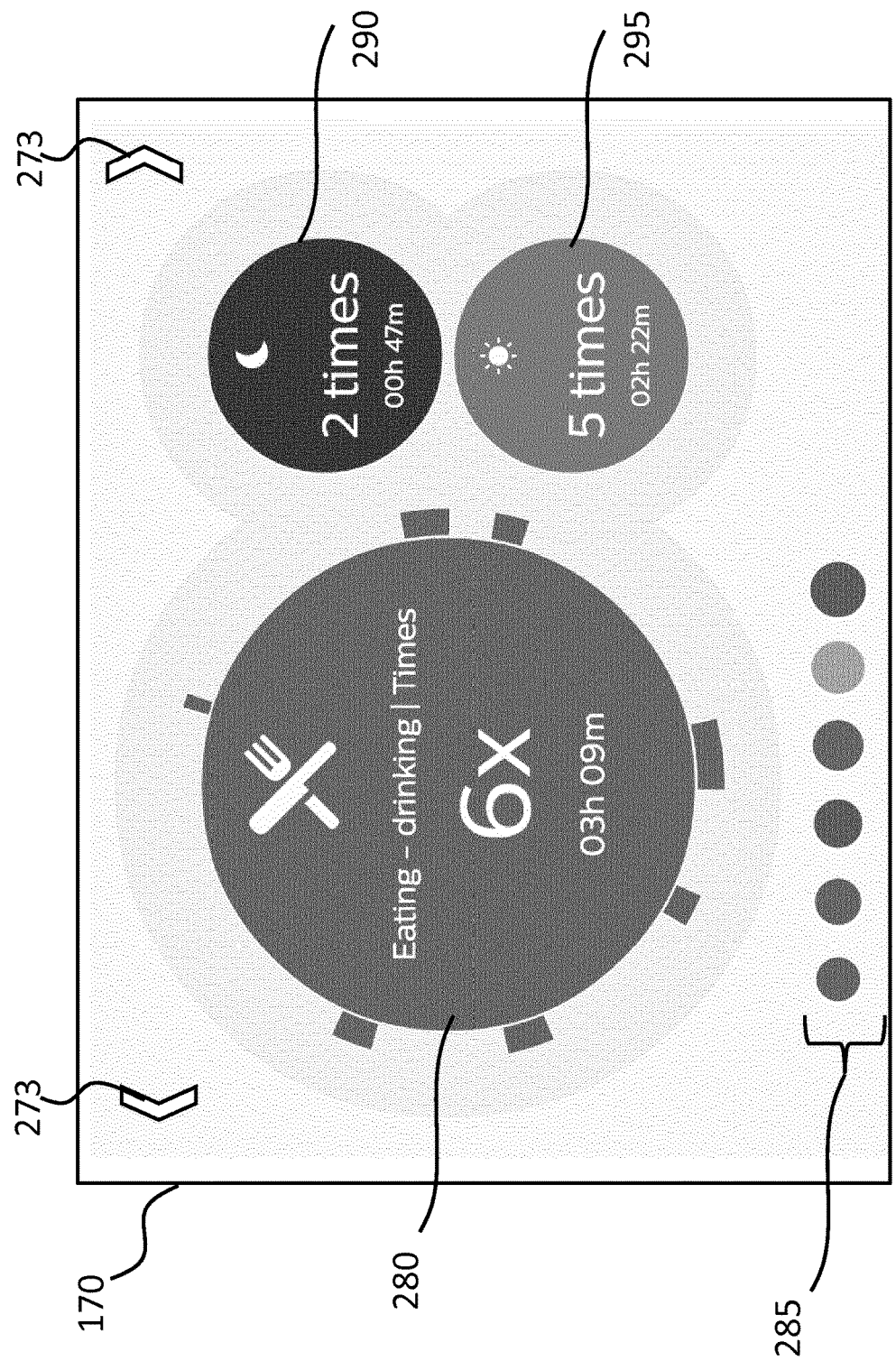
FIG. 4A is another exemplary displayed view of a GUI according to the invention.

FIG. 4A is another exemplary view of the display area 170 provided by the GUI 180 of FIG. 1 according to an embodiment. As described above, the display area 170 is adapted to display graphical elements in the display area 170. Here, first 280 to fourth 295 graphical elements are displayed in the display area.

The first graphical element 280 comprises a (relatively) large circle containing a symbol (of a knife and fork) and text providing a description of an ADL. In this example, the first graphical element 280 relates to eating and drinking instances that the monitored person has been detected as undertaking. Thus, the circle contains a written description of the ADL and numbers indicative of the cumulative number of eating/drinking instances the monitored person has been detected as undertaking during the current timeframe (e.g. the current day or today). It also contains an alphanumeric representation of the amount of time that has elapsed since the monitored person previously ate or drank.

It is also noted that the first graphical element 280 comprises a representation of the timing and duration of occurrences of eating/drinking instances. Each instance is depicted as a segment extending around the circumferential edge of the circle, wherein its position is representative of the timing of the instance and its length/size is representative of the duration of the instance.

Preferably, this is a timing over 24 hours, instead of 12 hours. In that way no overlap of instances occurs during a full day and night cycle and this improves situational awareness significantly for a viewer. Also, not shown in the Figure, there may be shading applied along segments of the circle that represent night time, day time or both. The shading can overlap with ADL instances. The start and finish of such shading may be pre-set or pre-programmed according to wintertime or summertime common night or day definitions, but preferably are user definable per person monitored using pre-set values for such start and ending. This can accommodate for the variability of ADL behaviour (e.g. sleeping behaviour) between different persons monitored. The presence of such shading gives an immediate impression on when ADLs have occurred. This may be important for assessment of sleeping behaviour for example.

The second graphical element 285 is positioned below the first graphical element 280 and comprises six circles, each representative of the number of eating/drinking instances the monitored person has been detected as undertaking during previous time periods (e.g. previous days of the week). Each circle of the second graphical element 285 comprises a particular colour that is indicative of the cumulative number of eating/drinking instances the monitored person was detected as undertaking during its associated/respective timeframe.

Thus, if the first graphical element 280 relates to a current day being Sunday, the six circles of the second graphical element 285 respectively relate to the preceding individual days of Saturday, Friday, Thursday, Wednesday, Tuesday and Monday. It will therefore be appreciated that the displayed first 280 and second 285 graphical elements of FIG. 4 display information relating to a monitored person's ADL of eating/drinking over the course of a current day and the preceding six days.

Also, the first 280 and second 285 graphical elements are displayed such that their size is representative of the nearness/proximity in time of the ADL (eating/drinking) In other words, a first graphical element 280 representative of a current day is displayed with a large size so that it is displayed with the most prominence, whereas the second graphical elements 285 representative of preceding (e.g. older) days are with a small size so that they are displayed with less prominence. Graphical elements representative of detected eating/drinking over the course of the week are therefore displayed, wherein the first graphical element 280 (which is representative of eating/drinking instances for the current day) is displayed with the largest size, and wherein the second graphical element 285 (which is representative of eating/drinking instances for the preceding six days of the week) is displayed with a smaller size. Nearness in time is therefore indicated by the size of the first 280 and second 285 graphical elements.

The third 290 and fourth 295 graphical elements are positioned to the right-hand of the first graphical element 280 and each respectively comprises a circle. The third graphical element 290 is representative of the number of eating/drinking instances the monitored person has been detected as undertaking during a night-time period of the current time period. The fourth graphical element 295 is representative of the number of eating/drinking instances the monitored person has been detected as undertaking during a day-time period of the current time period.

Each circle of the third 290 and fourth 295 graphical elements contains a symbolized description of the ADL and numbers indicative of the cumulative number of eating/drinking instances the monitored person has been detected as undertaking during the relevant. It also contains an alphanumeric representation of the amount of time that has elapsed since the monitored person previously ate or drank in the relevant time period. Furthermore, each circle comprises a particular colour that is indicative of the cumulative number of eating/drinking instances the monitored person was detected as undertaking during its associated/respective timeframe.

In this example, the displayed colour of the graphical elements is based on the cumulative number of eating/drinking instances. Thus, time period (e.g. days) during which the number of eating/drinking instances is abnormally high or low may be quickly and easily identified, since the respective graphical element(s) will be of a differing colour from the other graphical elements and therefore more prominent in the user's vision.

Graphical elements representative of detected eating/drinking instances over the course of the week are therefore displayed, wherein the graphical elements (which are representative of eating/drinking instances for a respective time period) are displayed with a colour indicative of a numerical value or range. A numerical value or range is therefore indicated by the colour of a displayed graphical element.

As displayed in the display area 272 of FIG. 3B are scroll handles 273 for scrolling through the displayed graphical elements. In this way, a viewer may scroll through the ADLs of different monitored persons. For example, if the multiple ADLs for a monitored person over a time period of a week, for example, are displayed as shown in FIG. 3B, activating (e.g. clicking or selecting) either of the scroll handles 273 may cause the displayed graphical elements to change such that the multiple ADLs to be navigated for different time periods, (e.g. previous or next days, weeks, months, etc.). The GUI 180 therefore enables a user to navigate through ADL information.

Although it has been explained that the scrolls handles 273 enable a user to scroll through ADL information for different time periods, alternative arrangements may enable ADL information for different monitored persons (e.g. Persons assigned to be observed by the user of the system) to be navigated (e.g. scrolled through).

Figure 4B:
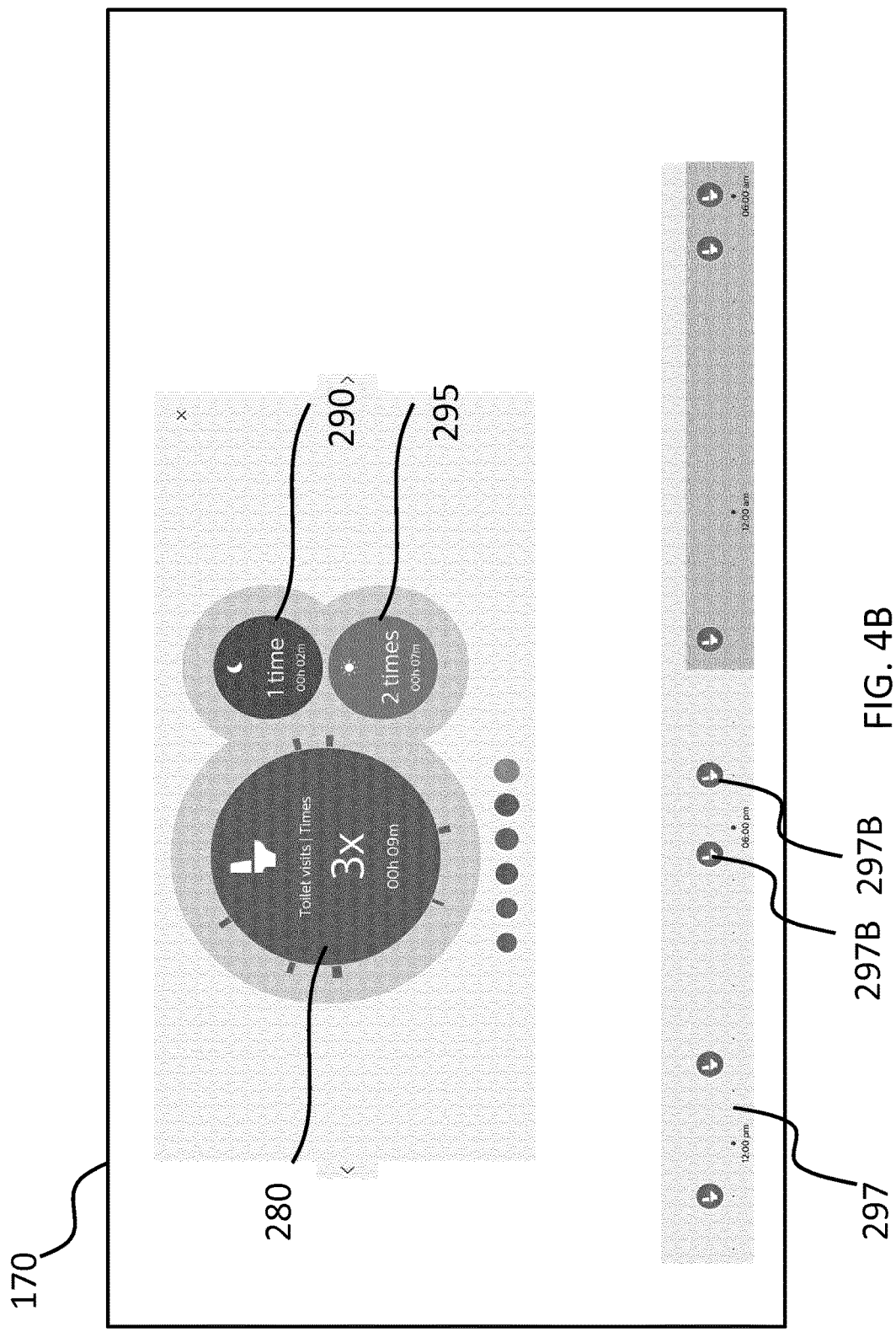
FIG. 4B depicts a modification to the displayed view of FIG. 4A.

FIG. 4B is another exemplary view of the display area 170 provided by the GUI 180 of FIG. 1 according to an embodiment. In particular, FIG. 4B shows a modification to the display area of FIG. 4A.

Similarly to FIG. 4A, the display area 170 of FIG. 4B is adapted to display first 280 to fourth 295 graphical elements in the display area 170. Since these first 280 to fourth 295 graphical elements are essentially the same as those described above for FIG. 4A. Accordingly, to avoid unnecessary repetition, description of the first 280 to fourth 295 graphical elements is omitted.

In addition to displaying the first 280 to fourth 295 graphical elements, the display area 170 of FIG. 4B is adapted to display a fifth graphical element 297.

The fifth graphical element 297 comprises a horizontally extending rectangle that spans the across the bottom of the display area (to the extent that is extends roughly 80-90% of the width of the display area 170). The fifth graphical element 297 represents a time line upon which occurrences of an ADL are identified by respective circles 297B. The relative positioning of a circle 297B within the fifth graphical element 297 indicates a time at which the respective ADL occurred.

The fifth graphical element may therefore be considered to provide a representation of a timeline wherein the provision of symbols along the timeline is synchronized with the occurrence(s) of an ADL (represented by the first graphical element 280, for example).

In this example, the displayed colour of the graphical elements is based on the cumulative number of toilet visit instances. Thus, a time period (e.g. days) during which the number of toilet visit instances is abnormally high or low may be quickly and easily identified, since the respective graphical element(s) will be of a differing colour from the other graphical elements and therefore more prominent in the user's vision.

Graphical elements representative of detected toilet visit instances over the course of the week are therefore displayed, wherein the graphical elements (which are representative of toilet visit instances for a respective time period) are displayed with a colour indicative of a numerical value or range. A numerical value or range is therefore indicated by the colour of a displayed graphical element. Also provided is a timeline representation of detected toilet visit instances over the course of a day such that the relative proximity of multiple instances can be quickly and easily interpreted.

Figure 4C:
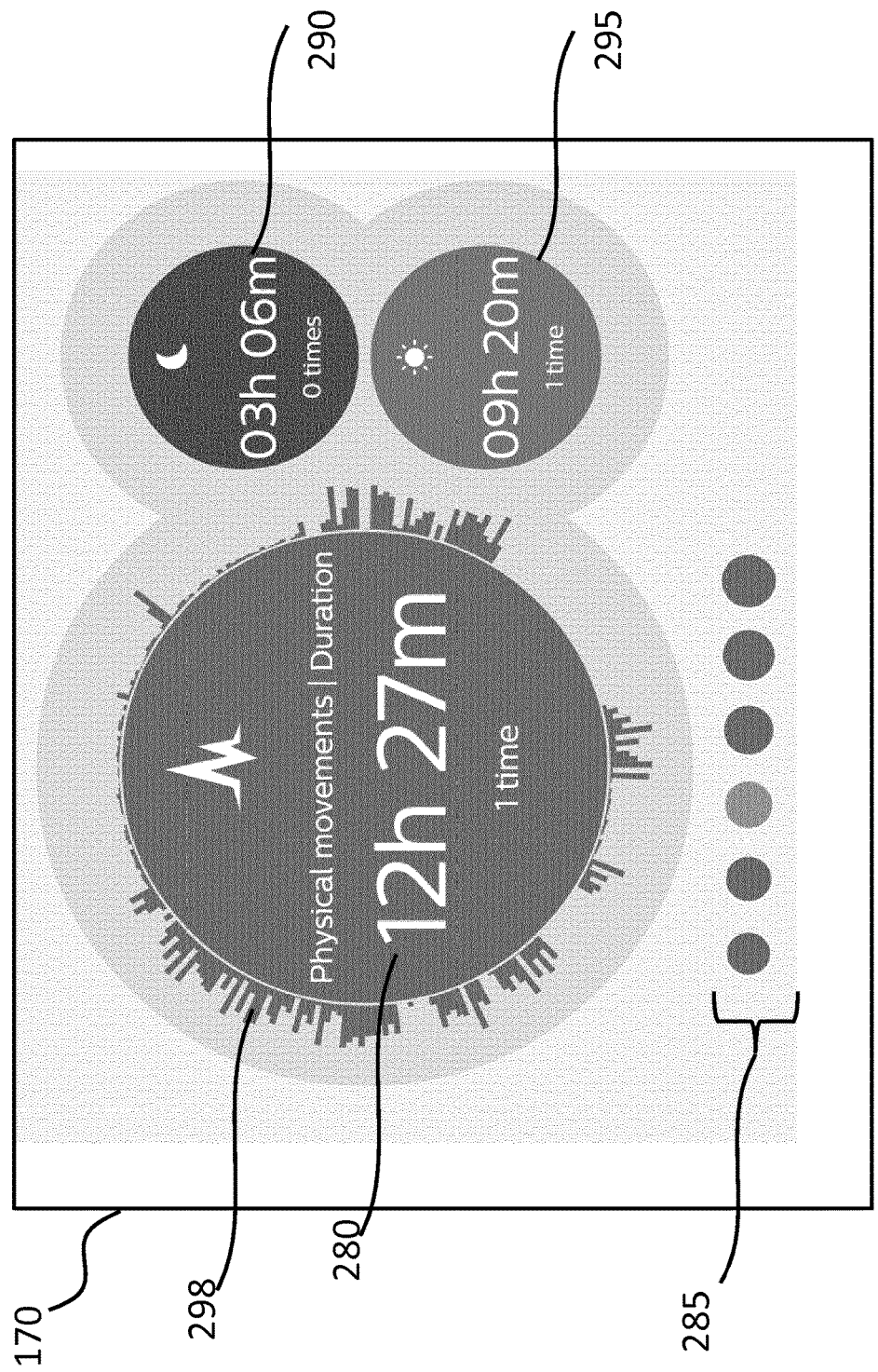
FIG. 4C depicts another modification to the displayed view of FIG. 4A.

FIG. 4C is yet another exemplary view of the display area 170 provided by the GUI 180 of FIG. 1 according to an embodiment. In particular, FIG. 4C shows a modification to the display area of FIG. 4A.

Similarly to FIG. 4A, the display area 170 of FIG. 4C is adapted to display first 280 to fourth 295 graphical elements in the display area 170. Since these first 280 to fourth 295 graphical elements are essentially the same as those described above for FIG. 4A. Accordingly, to avoid unnecessary repetition, description of the first 280 to fourth 295 graphical elements is omitted.

In addition to displaying the first 280 to fourth 295 graphical elements, the display area 170 of FIG. 4B is adapted to display a fifth graphical element 298 around the circumferential edge of the first graphical element 280.

The fifth graphical element 298 comprises bar-like elements extending outwardly from the circumferential edge of the first graphical element 280 in a radial direction. The fifth graphical element 297 represents a circumferential time line upon which occurrences of an ADL are identified by respective bar-like elements 298. The relative positioning of a bar-like element around the edge of the first graphical element 280 indicates a time at which the respective ADL occurred. Furthermore, the length (or amplitude) of a bar-like element indicates a value of the ADL. In this instance, wherein the ADL is "physical movement", the length (or amplitude) of a bar-like element is indicative of a detected intensity of the physical movement.

The fifth graphical element may therefore be considered to provide a representation of a circular timeline wherein the provision of bar-like elements along the timeline is synchronized with the occurrence(s) of an ADL (represented by the first graphical element 280, for example).

In this example, the displayed colour of the graphical elements is based on the cumulative number of physical activity instances. Thus, a time period (e.g. days) during which the number of physical activity instances is abnormally high or low may be quickly and easily identified, since the respective graphical element(s) will be of a differing colour from the other graphical elements and therefore more prominent in the user's vision.

Thus, in the example of FIG. 4C, graphical elements representative of detected physical movement instances over the course of the week are therefore displayed, wherein the graphical elements (which are representative of physical movement instances for a respective time period) are displayed with a colour indicative of a numerical value or range. Also provided is a circular timeline representation of detected physical activity instances (and their detected intensity) over the course of a day such that the time periods of zero physical activity and/or time periods of low/high physical activity can be quickly and easily identified.

Referring now to FIG. 5, there is depicted another embodiment of a ADL monitoring system according to the invention comprising a sensing system 510 arranged to measure a property of at least one of: the person; and the environment in which the person is.

Here, the sensing system 510 comprises a plurality of sensors adapted to detect one or values of at least one of: an ambient condition parameter of the environment; movement of the person that is monitored; and power consumption of an electrical appliance used by the person within the environment. The sensing system 510 is adapted to output one or more signals which are representative of the detected value(s).

The sensing system 510 communicates the output signals via the internet 520 (using a wired or wireless connection for example) to a remotely located data processing system 530 (such as server).

The data processing system 530 is adapted to receive the one or more output signals from the sensing system 510 and process the received signal(s) in accordance with an ADL inference/detection algorithm in order to infer/detect one or more ADLs of the monitored person. The data processing system 530 is further adapted to generate ADL output signals representative of inferred or detected ADLs of the person. Thus, the data processing 530 provides a centrally accessible processing resource that can receive information from the sensing system and run one or more algorithms to transform the received information into a set of detected or inferred ADLs. Information relating to the set of detected or inferred ADLs can be stored by the data processing system (for example, in an ADL database) and provided to other components of the ADL monitoring system. Such provision of information about detected or inferred ADLs may be undertaken in response to a receiving a request (via the internet 520 for example) and/or may be undertaken without request (i.e. 'pushed').

For the purpose of receiving information about detected or inferred ADLs from the data processing system, and thus to enable ADLs to be monitored, the system further comprises a first 540 and second 550 mobile computing device.

Here, the first mobile computing device 540 is a mobile telephone device (such as a smartphone) with a display for displaying graphical elements in accordance with embodiments of the proposed concepts. The second mobile computing device 550 is a mobile computer such as a Laptop or Tablet computer with a display for displaying graphical elements in accordance with embodiments of the proposed concepts.

The data processing system 530 is adapted to communicate ADL output signals to the first 540 and second 550 mobile computing devices via the internet 520 (using a wired or wireless connection for example). As mentioned above, this may be undertaken in response to receiving a request from the first 540 or second 550 mobile computing devices.

Based on the received ADL output signals, the first 540 and second 550 mobile computing devices are adapted to display one or more graphical elements in a display area provided by their respective display. For this purpose, the first 540 and second 550 mobile computing devices each comprise a software application for processing, decrypting and/or interpreting received ADL output signals in order to determine how to display graphical elements. Thus, the first 540 and second 550 mobile computing devices each comprise a processing arrangement adapted to determine an attribute of detected ADL, and to generate a display control signal for modifying at least one of the size, shape, position, orientation, pulsation or colour of the graphical element based on the determined attribute of the detected ADL.

The system can therefore communicate information about inferred or detected ADLs to users of the first 540 and second 550 mobile computing devices. For example, each of the first 540 and second 550 mobile computing devices may be used to display graphical elements to a medical practitioner, a caregiver, a family member or close relative.

Implementations of the system of FIG. 5 may vary between: (i) a situation where the data processing system 530 communicates display-ready ADL data, which may for example comprise display data including graphical elements (e.g. in JPEG or other image formats) that are simply displayed to a user of a mobile computing device using conventional image or webpage display (can be web based browser etc.); to (ii) a situation where the data processing system 530 communicates raw data set information that the receiving mobile computing device then transforms to ADL data, processes to determine one or more attributes of the ADL display, and then displays graphical elements based on the determined one or more attributes (for example, using local software running on the mobile computing device). Of course, in other implementations, the processing may be shared between the data processing system 530 and a receiving mobile computing device such that part of the ADL data generated at data processing system 530 is sent to the mobile computing device for further processing by local dedicated software of the mobile computing device. Embodiments may therefore employ server-side processing, client-side processing, or any combination thereof.

Further, where the data processing system 530 does not 'push' ADL information (e.g. ADL output signals), but rather communicates ADL information in response to receiving a request, the user of a device making such a request may be required to confirm or authenticate their identity and/or security credentials in order for ADL information to be communicated.

Figure 6:
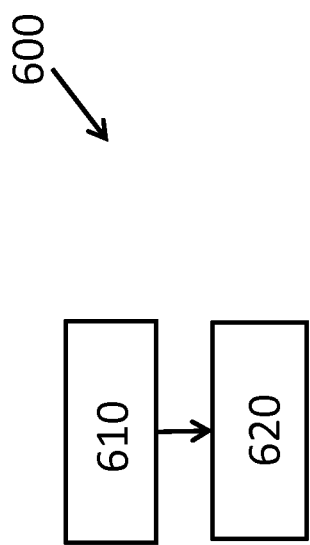
FIG. 6 shows a flow diagram of a method of generating a display for a GUI according to the invention.

Referring now to FIG. 6, there is shown a flow diagram of a method 600 of controlling an ADL monitoring system display device, wherein the ADL monitoring system display device comprises a display area adapted to a graphical element representative of an ADL detected by the ADL monitoring system.

The method begins with step 610 in which an attribute of the detected ADL is determined.

Then, in step 620, a control signal for modifying at least one of the size, shape, position, orientation, pulsation or colour of the graphical element is generated based on the determined attribute of the detected ADL. Here, the step 620 of generating a control signal comprises at least one of: comparing the determined attribute of the detected ADL with a first threshold value and generating the control signal so as to modify the colour of the graphical element to a first predetermined value if the determined attribute exceeds the first threshold value; and comparing the determined attribute of the detected ADL with a second threshold value and generating the control signal so as to modify the colour of the graphical element to a second predetermined value if the determined attribute is less than the second threshold value.

Thus, by way of example, by way of example, the method 600 of controlling an ADL monitoring system display device may be implemented in a portable computing device (such as the smartphone or portable computer shown in FIG. 5) in order to control the display of graphical elements on a display.

Figure 7:
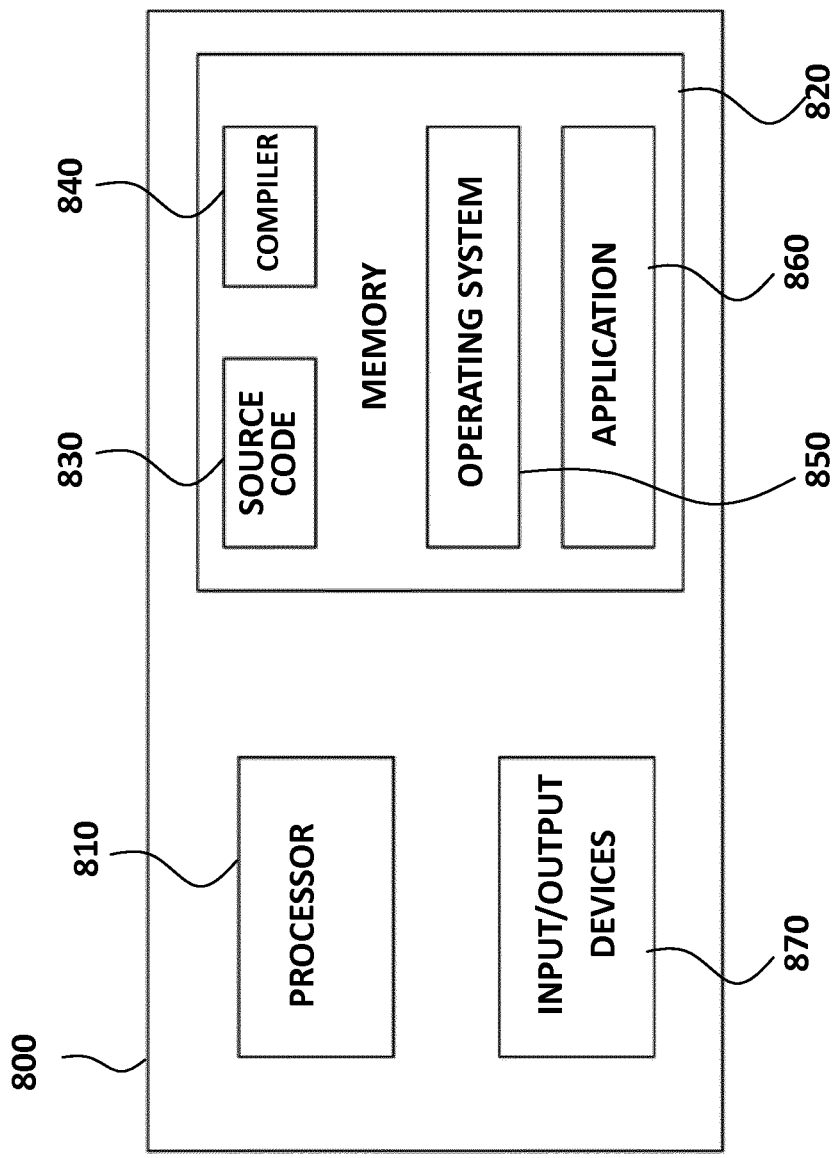
FIG. 7 is a block diagram of a computer (such as server device and/or client device) within which one or more parts of the invention can be performed.

FIG. 7 illustrates an example of a computer 800 within which one or more parts of an embodiment may be employed. The system can be or parts of the system can be such a computer. Various operations discussed above may utilize the capabilities of the computer 800. For example, one or more parts of an ADL monitoring system (or display device thereof) may be incorporated in any element, module, application, and/or component discussed herein.

The computer 800 includes, but is not limited to, Personal Computers, workstations, laptops, notebooks, tablets, mobile phones, smart phones, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a microprocessor.

The memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. It is contemplated by the inventors that the application 860 for implementing exemplary embodiments may be applicable on all commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 870 may include input devices such as, for example but not limited to, a mouse, keyboard, scanner, microphone, camera, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 860 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand various embodiments with various modifications are contemplated.

The invention claimed is:

1. A method of generating instructions for displaying a GUI on a display device using a processor device, which GUI is for monitoring of an Activities of Daily Living (ADL) of a person within an environment and comprises a plurality of graphical elements for representing the ADL at a respective plurality of different points in time, the graphical elements each being defined by at least a first graphical feature and a second graphical feature different from the first graphical feature, the method comprising:
the data processor device performing the steps of:
obtaining an attribute of the ADL for each of the plurality of different points in time;
defining the first graphical feature;
defining the second graphical feature, wherein the second graphical feature comprises a dimension of the graphical elements;
for each graphical element:
setting the first graphical feature based on the attribute of the ADL corresponding to a different one of the different points in time;
setting the second graphical feature based on the point in time corresponding to an attribute of the ADL upon which the setting of the first graphical feature of that particular element was based;
generating the instructions for displaying the GUI,
characterized wherein for the graphical element which represents the attribute of the ADL corresponding to the point in time that is nearest to a current time, the dimension of the second graphical feature of that graphical element is set to be larger than any dimension set of the respective graphical features for the other graphical elements of the plurality of elements, and the dimensions of the respective graphical features for the other graphical elements of the plurality of elements decrease with increasing time differences between the respective points in time and the current time.

2. The method of claim 1, wherein
the data processor device is performing the further steps of:
comparing the attribute of the ADL with a first threshold value;
setting the first graphical feature to a first feature value when the obtained attribute of the ADL is equal to or higher than the first threshold value, or
setting the first graphical feature to a second feature value different from the first feature value when the obtained attribute of the ADL is lower than the first threshold value.

3. The method of claim 1, wherein
the data processor device is performing the steps in a repeating fashion.

4. The method of claim 1, wherein each graphical element is defined by a third graphical feature, and wherein
the plurality of graphical elements comprises a main graphical element which represents the attribute of the ADL corresponding to the point in time that is nearest to current time;
the data processor device is performing the step of:
defining the third graphical feature to be position in the GUI;
setting the position of at least the plurality of graphical elements except the main graphical element such that they are arranged in the GUI in an array of graphical elements in the order of increasing or decreasing age with respect to current time of the attribute of the ADL they represent.

5. The method of claim 4, wherein
the processing device is performing the step of:
defining the array to be a linear array; and
orienting the array row wise and positioning the array next to and either above, or below the main graphical element, or orienting the array column wise and positioning the array next to and either on the left or on the right side of the main graphical element.

6. The method of claim 1, wherein
the processing device is performing the step of:
displaying a third graphical element around a circumferential edge of the graphical element which represents the attribute of the ADL corresponding to the point in time that is nearest to the current time, wherein the third graphical element represents a circumferential time line and comprises bar-shaped elements extending outwardly from the circumferential edge in a radial direction, and each of the bar-shaped elements has a length that represents a value of the ADL, at a different time.

7. The method of claim 1, wherein
the plurality of graphical elements comprises a main graphical element which represents the attribute of the ADL corresponding to the point in time that is nearest to current time;
the attribute of the ADL comprises an average or cumulative value of the attribute over a period of time;
the data processor device is performing the further steps of:
providing the attribute of the ADL represented by the main graphical feature also as an alphanumerical value.

8. The method of claim 1, wherein
the GUI is for monitoring a plurality of ADLs of the person;
the data processor device is performing the steps of:
obtaining an attribute of the plurality of ADLs of the person
for each one of the plurality of ADLs, arranging the one or more graphical elements representing that one ADL to be positioned within an ADL GUI area;
positioning the different ADL GUI areas within the GUI area such that they do not overlap at least partially.

9. The method of claim 8 wherein,
the step of positioning the different ADL GUI areas comprises positioning the different ADL GUI areas within the GUI in either row or column orientation.

10. The method of claim 1, wherein
the data processor device comprising the step of:
obtaining identification data for identifying the person and corresponding to the ADL represented by the graphical elements of the ADL;
adding the identification data to the GUI to enable a user to identify the person that the graphical elements of an ADL belong to.

11. The method of claim 1, further comprising:
executing the instructions for displaying the GUI, which causes a display device to display the GUI.

12. The method of claim 1, wherein
the data processor is performing the steps of:
obtaining user input in the form of input device signal to switch from a first GUI screen comprising ADL data of a plurality of persons to a GUI screen showing ADL data of a particular one person of the plurality of persons, or to show ADL data of a particular one person of the plurality of persons in a further GUI window.

13. The method of claim 1, wherein
the processing device is performing the step of:
  displaying the graphical element which represents the attribute of the ADL corresponding to the point in time that is nearest to the current time above the other graphical elements; and
  displaying second and third graphical elements next to the graphical element corresponding to the point in time nearest to the current time and above the other graphical elements,
  wherein the second graphical element indicates a value of the attribute of the ADL corresponding to the point in time that is nearest to the current time during a day time period,
  wherein the third graphical element indicates a value of the attribute of the ADL corresponding to the point in time that is nearest to the current time during a night time period, and
  wherein the second graphical element is above the third graphical element.

14. A non-transitory computer readable medium configured to store a computer program product downloadable from a communications network wherein the computer program product comprises computer program code instructions, which when executed on a computer, causes the computer to:
  obtain an attribute of an Activities of Daily Living (ADL) of a person within an environment for each of a plurality of different points in time;
  define a first graphical feature;
  define a second graphical feature, wherein the second graphical feature comprises dimension of graphical elements for representing the ADL over the plurality of different points in time;
  set, for each of the graphical elements, the first graphical feature based on the attribute of the ADL corresponding to a different one of the different points in time;
  set, for each of the graphical elements, the second graphical feature based on the point in time corresponding to an attribute of the ADL upon which the setting of the first graphical feature of that particular element was based; and
  generate instructions for displaying a GUI on a display device, which GUI is for monitoring of the ADL,
  wherein for the graphical element which represents the attribute of the ADL corresponding to the point in time that is nearest to a current time, the dimension of the second graphical feature of that graphical element is set to be larger than any dimension set of the respective graphical features for the other graphical elements of the plurality of elements, and
  wherein for the graphical element which represents the attribute of the ADL corresponding to the point in time that is farthest from the current time, the dimension of the second graphical feature of that graphical element is set to be smaller than any dimension set of the respective graphical features for the other graphical elements of the plurality of elements.

15. A system configured to generate instructions for displaying a GUI on a display device using a processor device, which GUI is for monitoring of an Activities of Daily Living (ADL) of a person within an environment and comprises a plurality of graphical elements for representing the ADL at a respective plurality of different points in time, the graphical elements each being defined by at least a first graphical feature and a second graphical feature different from the first graphical feature, the system comprising the data processor device, wherein:
  the data processor device is configured to:
    obtain an attribute of the ADL for each of the plurality of different points in time;
    define the first graphical feature;
    define the second graphical feature, wherein the second graphical feature comprises a dimension of the graphical element;
    for each graphical element:
      set the first graphical feature based on the attribute of the ADL corresponding to a different on of the different points in time;
      set the second graphical feature based on the point in time corresponding to an attribute of the ADL upon which the setting of the first graphical feature of that particular element was based;
    generate the instructions for displaying the GUI,
  wherein for the graphical element which represents the attribute of the ADL corresponding to the point in time that is nearest to the current time, the dimension of the second graphical feature of that graphical element is set to be larger than any dimension set of the respective graphical features for the other graphical elements of the plurality of elements,
  wherein for the graphical element which represents the attribute of the ADL corresponding to the point in time that is farthest to the current time, the dimension of the second graphical feature of that graphical element is set to be smaller than any dimension set of the respective graphical features for the other graphical elements of the plurality of elements, and
  wherein for the graphical elements which represent the attributes of the ADL corresponding to points in time between the nearest and farthest times to the current time, the dimensions of the second graphical features of those graphical elements decrease in size from the nearest and farthest times to the current time.

16. The system of claim 15, wherein
the data processor device is configured to:
  compare the attribute of the ADL with a first threshold value;
  set the first graphical feature to a first feature value if the obtained attribute of the ADL is equal to or higher than the first threshold value, or
  set the first graphical feature to a second feature value different from the first feature value if the obtained attribute of the ADL is lower than the first threshold value.

17. The system of claim 15, wherein
the data processor device is configured to:
  perform the steps in a repeating fashion.

18. The system of claim 15, wherein each graphical element is defined by a third graphical feature, and wherein the plurality of graphical elements comprises a main graphical element which represents the attribute of the ADL corresponding to the point in time that is nearest to current time;
the data processor device is configured to:
  define the third graphical feature to be the position in the GUI;
  set the position of at least the plurality of graphical elements except the main graphical element such that they are arranged in the GUI in an array of graphical elements in the order of increasing or decreasing age with respect to current time of the attribute of the ADL they represent.

19. The system of claim 18, wherein
the processing device is configured to:
  define the array to be a linear array; and
  orient the array row wise and position the array next to and either above, or below the main graphical element, or
  orient the array column wise and position the array next to and either on the left or on the right side of the main graphical element.

20. The system of claim 15, wherein the first graphical element is circular in shape.

21. The system of claim 15, wherein
the plurality of graphical elements comprises a main graphical element which represents the attribute of the ADL corresponding to the point in time that is nearest to current time;
the attribute of the ADL comprises an average or cumulative value of the attribute over a period of time;
the data processor device is configured to:
  provide the attribute of the ADL represented by the main graphical feature also as an alphanumerical value.

22. The system of claim 15, wherein
the GUI is for monitoring a plurality of ADLs of the person;
the data processor device is configured to:
  obtain an attribute of the plurality of ADLs of the person
  for each one of the plurality of ADLs, arrange the one or more graphical elements representing that one ADL to be positioned within an ADL GUI area;
  position the different ADL GUI areas within the GUI area such that they do not overlap at least partially.

23. The system of claim 22 wherein,
to position the different ADL GUI areas comprises to position the different ADL GUI areas within the GUI in either row or column orientation.

24. The system of claim 15, wherein
the data processor device is configured to:
  obtain identification data for identifying the person and corresponding to the ADL represented by the graphical elements of the ADL;
  add the identification data to the GUI to enable a user to identify the person that the graphical elements of an ADL belong to.

25. The system of claim 15, wherein the data processor device is further configured to
display the GUI based on the generated instructions.

26. The system of claim 25, comprising:
a server device comprising the data processor device;
a client device comprising the display device;
wherein
the server device is configured to transmit the generated instructions for display of the GUI to the remote client device;
the remote client device is configured to receive the generated instructions for display of the GUI and to use the instructions to display the GUI.

27. The system of claim 25, comprising
a client device comprising the data processor device and the display device.

28. The system of claim 15, comprising:
a server device comprising the data processor device and the configured to:
  transmit the generated instructions for display of the GUI to a client device or communication network.

* * * * *